United States Patent
Zhao et al.

(10) Patent No.: US 11,254,746 B2
(45) Date of Patent: Feb. 22, 2022

(54) ANTI-PD-1 MONOCLONAL ANTIBODY, AND PREPARATION METHOD THEREFOR AND APPLICATION THEREOF

(71) Applicant: SUNSHINE GUOJIAN PHARMACEUTICAL (SHANGHAI) CO., LTD., Shanghai (CN)

(72) Inventors: Jie Zhao, Shanghai (CN); Honghai Gao, Shanghai (CN); Jinlin Guo, Shanghai (CN); Wei Dang, Shanghai (CN); Lingqiao Zhu, Shanghai (CN); Chenghai Zhang, Shanghai (CN); Le Zhao, Shanghai (CN); Jianhe Chen, Shanghai (CN); Haomin Huang, Shanghai (CN); Zhenping Zhu, Shanghai (CN)

(73) Assignee: SUNSHINE GUOJIAN PHARMACEUTICAL (SHANGHAI) CO., LT, Shanghai (CN)

( * ) Notice: Subject to any disclaimer, the term of this patent is extended or adjusted under 35 U.S.C. 154(b) by 33 days.

(21) Appl. No.: 16/480,014

(22) PCT Filed: Jan. 22, 2018

(86) PCT No.: PCT/CN2018/073575
§ 371 (c)(1),
(2) Date: Sep. 12, 2019

(87) PCT Pub. No.: WO2018/137576
PCT Pub. Date: Aug. 2, 2018

(65) Prior Publication Data
US 2020/0377597 A1    Dec. 3, 2020

(30) Foreign Application Priority Data
Jan. 24, 2017 (CN) .......................... 201710054783.5

(51) Int. Cl.
| | | |
|---|---|---|
| A61K 39/00 | (2006.01) |
| A61K 39/395 | (2006.01) |
| C07K 16/00 | (2006.01) |
| C07K 16/46 | (2006.01) |
| C07H 21/04 | (2006.01) |
| C12P 21/06 | (2006.01) |
| C12N 15/87 | (2006.01) |
| C12N 1/20 | (2006.01) |
| C12N 15/74 | (2006.01) |
| C07K 16/28 | (2006.01) |
| A61P 35/00 | (2006.01) |

(52) U.S. Cl.
CPC .......... *C07K 16/2818* (2013.01); *A61P 35/00* (2018.01); *A61K 2039/505* (2013.01); *C07K 2317/24* (2013.01); *C07K 2317/56* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 8,735,553 B1 | 5/2014 | Li et al. | |
| 10,414,821 B2 | 9/2019 | Liu | |
| 10,577,422 B2 * | 3/2020 | Shah | ........................ A61P 1/16 |
| 2015/0210769 A1 | 7/2015 | Freeman et al. | |
| 2019/0071501 A1 | 3/2019 | Li et al. | |

FOREIGN PATENT DOCUMENTS

| | | |
|---|---|---|
| CN | 105330740 A | 2/2016 |
| CN | 106008714 | 10/2016 |
| CN | 106336460 A | 1/2017 |
| EP | 3081576 | 10/2016 |
| WO | WO 2008/156712 | 12/2008 |
| WO | WO 2013169693 | 11/2013 |
| WO | WO 2014194302 | 2/2015 |
| WO | WO 2015112900 | 7/2015 |
| WO | WO 2016/014688 | 1/2016 |
| WO | WO 2017/011580 | 1/2017 |
| WO | WO 2017/058115 | 4/2017 |

OTHER PUBLICATIONS

F. Ausubel et al., Current Protocols in Molecular Biology, Dec. 4, 2003, 1-2499 pages, John Wiley & Sons Inc, ringbou edition, Hoboken, NJ.
J.Sambrook et al., Molecular cloning: a laboratory manual—Abstract, 1989, 1 page, Ed. 2, University of Texas South Western Medical Center, Dallas, Texas.
International Search Report dated Apr. 17, 2018, 5 pages, China.
X. Zhang, et al., Structural and Functional Analysis of the Costimulatory Receptor Programmed Death-1, Immunity, vol. 20, Mar. 2004, pp. 337-347, Cell Press, Cambridge, MA.
C. Blank et al., Interaction of PD-L1 on tumor cells with PD-1 on tumor-specific T cells as a mechanism of immune evasion: implications for tumor immunotherapy. Cancer Immunol Immunother 54, 307-314 (2005). https://doi.org/10.1007/s00262-004-0593-x.

(Continued)

*Primary Examiner* — Maher M Haddad
(74) *Attorney, Agent, or Firm* — Thorpe North & Western

(57) ABSTRACT

An anti-human PD-1 monoclonal antibody, and a preparation method therefor and an application thereof. The anti-human PD-1 monoclonal antibody has good bioactivity, can effectively bind with an extracellular region of a human PD-1 protein receptor, and can effectively seal PD-1 protein at protein level and cellular level and block the binding of the PD-1 protein with a ligand PD-L1, thereby effectively enhancing immunity. The monoclonal antibody can be applied independently or jointly with other antitumor drugs to tumor immunotherapy and the diagnosis and screening of patients with PD-L1 positive tumors; and the monoclonal antibody has a promising prospect in the preparation of drugs for treating tumors, resisting autoimmune diseases and the like.

23 Claims, 3 Drawing Sheets
Specification includes a Sequence Listing.

(56) References Cited

OTHER PUBLICATIONS

D. Lin et al., The PD-1/PD-L1 complex resembles the antigen-binding Fv domains of antibodies and T cell receptors, Proceedings of the National Academy of Sciences, Feb. 26, 2008, pp. 3011-30116, 105(8), published online www.pnas.org/cgi/doi/10.1073/pnas.0712278105.
S. Strome et al., B7-H1 Blockade Augments Adoptive T-Cell Immunotherapy for Squamous Cell Carcinoma, Cancer Research, Oct. 2003, pp. 6501-6505, vol. 63, Issue 19, American Association for Cancer Research, Rochester, Minnesota.
Y. Iwai et al., Involvement of PD-L1 on tumor cells in the escape from host immune system and tumor immunotherapy by PD-L1 blockade, Proceedings of the National Academy of Sciences, Sep. 17, 2002, pp. 12293-12297, vol. 9, No. 19, published online www.pnas.org/cgi/doi/10.1073/pnas.192461099.

\* cited by examiner

SEQUENCE LISTING

<160> NUMBER OF SEQ ID NOS: 40

<210> SEQ ID NO 1
<211> LENGTH: 5
<212> TYPE: PRT
<213> ORGANISM: Artificial
<220> FEATURE:
<223> OTHER INFORMATION: A sequence of CDRH1

<400> SEQUENCE: 1

Ser Tyr Asp Met Ser
1               5

<210> SEQ ID NO 2
<211> LENGTH: 17
<212> TYPE: PRT
<213> ORGANISM: Artificial
<220> FEATURE:
<223> OTHER INFORMATION: A sequence of CDRH2

<400> SEQUENCE: 2

Thr Ile Ser Gly Gly Gly Arg Tyr Thr Tyr Tyr Pro Asp Thr Val Lys
1               5                   10                  15

Gly

<210> SEQ ID NO 3
<211> LENGTH: 8
<212> TYPE: PRT
<213> ORGANISM: Artificial
<220> FEATURE:
<223> OTHER INFORMATION: A sequence of CDRH3

<400> SEQUENCE: 3

Pro Tyr Gly Gly Tyr Phe Asp Val
1               5

<210> SEQ ID NO 4
<211> LENGTH: 11
<212> TYPE: PRT
<213> ORGANISM: Artificial
<220> FEATURE:
<223> OTHER INFORMATION: A sequence of CDRL1

<400> SEQUENCE: 4

Arg Ala Ser Gln Ser Ile Ser Asn Phe Leu His
1               5                   10

<210> SEQ ID NO 5
<211> LENGTH: 7
<212> TYPE: PRT
<213> ORGANISM: Artificial
<220> FEATURE:
<223> OTHER INFORMATION: A sequence of CDRL2

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Artificial
<220> FEATURE:
<223> OTHER INFORMATION: A sequence of CDRL3

<400> SEQUENCE: 6

Gln Gln Ser Asn Ser Trp Pro His Thr
1               5

<210> SEQ ID NO 7
<211> LENGTH: 117
<212> TYPE: PRT
<213> ORGANISM: Artificial
<220> FEATURE:
<223> OTHER INFORMATION: Heavy chain variable region amino acid sequence
      of mAb1-25-Humanized

<400> SEQUENCE: 7

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Thr Ile Ser Gly Gly Gly Arg Tyr Thr Tyr Tyr Pro Asp Thr Val
    50                  55                  60

Lys Gly Arg Phe Thr Ile Ser Arg Asp Asn Ala Lys Asn Ser His Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Gly Tyr Phe Asp Val Trp Gly Gln Gly Thr Leu
            100                 105                 110

Val Thr Val Ser Ser
            115
```

<210> SEQ ID NO 8
<211> LENGTH: 444
<212> TYPE: PRT
<213> ORGANISM: Artificial
<220> FEATURE:
<223> OTHER INFORMATION: Heavy chain full length amino acid sequence of mAb1-25-Humanized

<400> SEQUENCE: 8

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Ala Phe Ser Ser Tyr
            20                  25                  30

Asp Met Ser Trp Val Arg Gln Ala Pro Gly Lys Arg Leu Glu Trp Val
        35                  40                  45

Ala Thr Ile Ser Gly Gly Gly Arg Tyr Thr Tyr Tyr Pro Asp Thr Val
    50                  55                  60

Lys Gly Arg Phe Thr Ile Ser Arg Asp Asn Ala Lys Asn Ser His Tyr
65                  70                  75                  80

Leu Gln Met Asn Ser Leu Arg Ala Glu Asp Thr Ala Val Tyr Phe Cys
                85                  90                  95

Ala Ser Pro Tyr Gly Gly Tyr Phe Asp Val Trp Gly Gln Gly Thr Leu
            100                 105                 110

Val Thr Val Ser Ser Ala Ser Thr Lys Gly Pro Ser Val Phe Pro Leu
            115                 120                 125

Ala Pro Cys Ser Arg Ser Thr Ser Glu Ser Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220
```

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
        260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 9
<211> LENGTH: 107
<212> TYPE: PRT
<213> ORGANISM: Artificial
<220> FEATURE:
<223> OTHER INFORMATION: Light chain variable region amino acid sequence
      of mAb1-25-Humanized

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Phe
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro His
                85                  90                  95

Thr Phe Gly Gln Gly Thr Lys Val Glu Ile Lys
            100                 105

<210> SEQ ID NO 10
<211> LENGTH: 214
<212> TYPE: PRT

<213> ORGANISM: Artificial
<220> FEATURE:
<223> OTHER INFORMATION: Light chain full length amino acid sequence of mAb1-25-Humanized

<400> SEQUENCE: 10

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Phe
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro His
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 1332
<212> TYPE: DNA
<213> ORGANISM: Artificial
<220> FEATURE:
<223> OTHER INFORMATION: Heavy chain nucleotide sequence of mAb1-25-Humanized

<400> SEQUENCE: 11

```
gaagtcaaac tcgtggagtc cggcggaggc ctcgttcaac caggtggatc tcttcgtttg    60
tcctgcgcag catcaggatt cgctttctcc agctacgaca tgagctgggt ccgacaggct   120
cctggaaaga ggctgaatg ggttgctact atcagcggcg gtggtagata tacttattac    180
cccgataccg taaagggag gttcaccatt agtcgcgata cgccaaaaa ttcacactac     240 ctgcagatga actctctgcg ggccgaggac accgccgtgt acttttgtgc cagtccctat   300
ggcgggtatt ttgacgtgtg gggccagggg acactggtga ctgtgagttc tgcaagtacc   360
aagggaccta gtgttttccc tcttgcacct tgctccaggt caacatcaga gtccacagct   420
gctcttggat gtctcgttaa ggactacttc ccagagccag ttaccgtatc ctggaactcc   480
ggagctttga caagcggcgt tcatacattc ccagctgtgt tgcagagttc tgggttgtac   540
agtttgagct cagtggtgac cgtgccttca tcttctttgg gcactaagac ctacacctgc   600
```

```
aacgtggatc acaagccaag caacaccaag gtggataaga gggtggagtc caagtacggc    660
ccaccatgtc ctccatgtcc agcccctgaa tttttgggcg ggccttctgt ctttctgttt    720
cctcctaaac ctaaagatac cctgatgatc agccgcacac ccgaagtcac ttgtgtggtc    780
gtggatgtgt ctcaggaaga tcccgaagtg cagtttaact ggtatgtcga tggcgtggaa    840
gtgcataatg ccaaaactaa gccccgcgaa gaacagttca acagcactta tcgggtcgtg    900
tctgtgctca cagtcctcca tcaggattgg ctgaatggga agaatataa gtgcaaggtg    960 agcaataagg gcctccccag cagcatcgag aagactatta gcaaagccaa agggcagcca   1020 cgggaaccc agtgtacac tctgcccccc tctcaggagg agatgactaa aaatcaggtc   1080
tctctgactt gtctggtgaa agggttttat cccagcgaca ttgccgtgga gtgggagtct   1140
aatggccagc ccgagaataa ttataagaca actcccccg tcctggactc tgacggcagc   1200 ttttttcctgt attctcggct gacagtggac aaaagtcgct ggcaggaggg caatgtcttt   1260
agttgcagtg tcatgcatga ggccctgcac aatcactata cacagaaaag cctgtctctg   1320
agtctgggca aa                                                      1332

<210> SEQ ID NO 12
<211> LENGTH: 642
<212> TYPE: DNA
<213> ORGANISM: Artificial
<220> FEATURE:
<223> OTHER INFORMATION: Light chain nucleotide sequence of mAb1-25-
      Humanized

<400> SEQUENCE: 12
gagatcgtcc ttacccaatc accagcaacc ttgtcactgt caccaggtga aagagcaacc     60
ctcagttgta gggctagtca gagtatctcc aacttcctgc actggtacca gcagaagcct    120
ggacaggccc ctcggttgct cattaagtac gcctctcaat ctatcagcgg aatccccgct    180
cgcttttctg gctctggctc cgggactgat ttcactctga caatttccag cctgaaccc    240 gaggactttg ccgtttattt ttgccagcag agcaatagct ggccccatac attcgggcag    300
ggcacaaaag tggagataaa acgcactgtg gctgcccca gtgttttcat atttccccc    360 agtgatgagc aactgaagtc cggcacagcc tctgttgtat gtctgctgaa taatttttat    420
ccacgggagg ccaaggtgca gtggaaggtg acaatgccc tgcagtctgg gaactctcaa    480
gagagtgtga cagagcagga cagtaaagac agcacctata gcctcagcag cacccctgacc    540 ctgtctaaag ccgactatga aaacacaaa gtgtatgcct gcgaagtgac ccatcagggg    600
ctcagctctc ccgttaccaa gagctttaac cgaggcgaat gt                      642

<210> SEQ ID NO 13
<211> LENGTH: 5
<212> TYPE: PRT
<213> ORGANISM: Artificial
<220> FEATURE:
<223> OTHER INFORMATION: Another sequence of CDRH1

<400> SEQUENCE: 13

Ser Tyr Asp Met Ser
1               5

<210> SEQ ID NO 14
<211> LENGTH: 17
<212> TYPE: PRT
<213> ORGANISM: Artificial
<220> FEATURE:
```

<223> OTHER INFORMATION: Another sequence of CDRH2

<400> SEQUENCE: 14

Thr Ile Ser Gly Gly Gly Arg Tyr Thr Tyr Tyr Pro Asp Ser Val Lys
1               5                   10                  15
Gly

<210> SEQ ID NO 15
<211> LENGTH: 9
<212> TYPE: PRT
<213> ORGANISM: Artificial
<220> FEATURE:
<223> OTHER INFORMATION: Another sequence of CDRH3

<400> SEQUENCE: 15

Arg Tyr Asp Val Asp Trp Phe Ala Tyr
1               5

<210> SEQ ID NO 16
<211> LENGTH: 11
<212> TYPE: PRT
<213> ORGANISM: Artificial
<220> FEATURE:
<223> OTHER INFORMATION: Another sequence of CDRL1

<400> SEQUENCE: 16

Arg Ala Ser Gln Ser Ile Ser Asn Asn Leu His
1               5                   10

<210> SEQ ID NO 17
<211> LENGTH: 7
<212> TYPE: PRT
<213> ORGANISM: Artificial
<220> FEATURE:
<223> OTHER INFORMATION: Another sequence of CDRL2

<400> SEQUENCE: 17

Tyr Ala Ser Gln Ser Ile Ser
1               5

<210> SEQ ID NO 18
<211> LENGTH: 9
<212> TYPE: PRT
<213> ORGANISM: Artificial
<220> FEATURE:
<223> OTHER INFORMATION: Another sequence of CDRL3

<400> SEQUENCE: 18

Gln Gln Ser Asn Ser Trp Pro Leu Thr
1               5

<210> SEQ ID NO 19
<211> LENGTH: 118
<212> TYPE: PRT
<213> ORGANISM: Artificial
<220> FEATURE:
<223> OTHER INFORMATION: Heavy chain variable region amino acid sequence
      of mAb1-15-humanized

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Arg Leu Glu Trp Val

```
                35                  40                  45
Ala Thr Ile Ser Gly Gly Arg Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Asn Arg Tyr Asp Val Asp Trp Phe Ala Tyr Trp Gly Gln Gly Thr
                100                 105                 110

Leu Val Thr Val Ser Ser
        115

<210> SEQ ID NO 20
<211> LENGTH: 445
<212> TYPE: PRT
<213> ORGANISM: Artificial
<220> FEATURE:
<223> OTHER INFORMATION: Heavy chain full length amino acid sequence of
      mAb1-15-humanized

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Asp Met Ser Trp Val Arg Gln Ala Pro Gly Lys Arg Leu Glu Trp Val
                35                  40                  45

Ala Thr Ile Ser Gly Gly Arg Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Asn Arg Tyr Asp Val Asp Trp Phe Ala Tyr Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270
```

```
Phe Asn Trp Tyr Val Asp Gly Val Glu Val His Asn Ala Lys Thr Lys
            275                 280                 285
Pro Arg Glu Glu Gln Phe Asn Ser Thr Tyr Arg Val Val Ser Val Leu
        290                 295                 300
Thr Val Leu His Gln Asp Trp Leu Asn Gly Lys Glu Tyr Lys Cys Lys
305                 310                 315                 320
Val Ser Asn Lys Gly Leu Pro Ser Ser Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Gln Glu Glu Met Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Arg Leu Thr Val Asp Lys Ser Arg Trp Gln
                405                 410                 415
Glu Gly Asn Val Phe Ser Cys Ser Val Met His Glu Ala Leu His Asn
            420                 425                 430
His Tyr Thr Gln Lys Ser Leu Ser Leu Ser Leu Gly Lys
            435                 440                 445

<210> SEQ ID NO 21
<211> LENGTH: 107
<212> TYPE: PRT
<213> ORGANISM: Artificial
<220> FEATURE:
<223> OTHER INFORMATION: Light chain variable region amino acid sequence
      of mAb1-15-humanized

<400> SEQUENCE: 21

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Ile Ser Asn Asn
            20                  25                  30
Leu His Trp Tyr Gln Gln Lys Pro Gly Gln Ala Pro Arg Leu Leu Ile
        35                  40                  45
Lys Tyr Ala Ser Gln Ser Ile Ser Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Phe Cys Gln Gln Ser Asn Ser Trp Pro Leu
                85                  90                  95
Thr Phe Gly Gln Gly Thr Lys Val Glu Ile Lys
            100                 105

<210> SEQ ID NO 22
<211> LENGTH: 214
<212> TYPE: PRT
<213> ORGANISM: Artificial
<220> FEATURE:
<223> OTHER INFORMATION: Light chain full length amino acid sequence of
      mAb1-15-humanized

<400> SEQUENCE: 22

Glu Ile Val Leu Thr Gln Ser Pro Ala Thr Leu Ser Leu Ser Pro Gly
1               5                   10                  15
```

```
Glu Arg Ala Thr Leu Ser Cys Arg Ala Ser Gln Ser Ile Ser Asn Asn
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Phe Cys Gln Gln Ser Asn Ser Trp Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 354
<212> TYPE: DNA
<213> ORGANISM: Artificial
<220> FEATURE:
<223> OTHER INFORMATION: Heavy chain variable region nucleotide sequence
      of mAb1-15

<400> SEQUENCE: 23
gaagtgaacc tggtggagtc tgggggaggc ttagtgaagc ctggagggtc cctgaaactc      60
tcctgtgcag cctctggatt cactttcagt agctatgaca tgtcttgggt tcgccagact     120
ccggagaaga ggctggagtg ggtcgcaacc attagtggtg gtggtcgtta cacctattat     180
ccagacagtg tgaagggccg attcaccatc tccagagaca atgccaagaa caacctgtac     240
ctgcaaatga gcagtctgag gtctgaggac acggccttgt attactgtgc aaataggtac     300
gacgtggact ggtttgctta ctggggccaa gggactctgg tcactgtctc tgca           354

<210> SEQ ID NO 24
<211> LENGTH: 118
<212> TYPE: PRT
<213> ORGANISM: Artificial
<220> FEATURE:
<223> OTHER INFORMATION: Heavy chain variable region amino acid sequence
      of mAb1-15

<400> SEQUENCE: 24

Glu Val Asn Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30
```

Asp Met Ser Trp Val Arg Gln Thr Pro Glu Lys Arg Leu Glu Trp Val
35                  40                  45

Ala Thr Ile Ser Gly Gly Arg Tyr Thr Tyr Tyr Pro Asp Ser Val
50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
            85                  90                  95

Ala Asn Arg Tyr Asp Val Asp Trp Phe Ala Tyr Trp Gly Gln Gly Thr
            100                 105                 110

Leu Val Thr Val Ser Ala
        115

<210> SEQ ID NO 25
<211> LENGTH: 321
<212> TYPE: DNA
<213> ORGANISM: Artificial
<220> FEATURE:
<223> OTHER INFORMATION: Light chain variable region nucleotide sequence
      of mAb1-15

<400> SEQUENCE: 25
gatattgtgc taactcagtc tccagccacc ctgtctgtga ctccaggaga tagcgtcagt    60
ctttcctgca gggccagcca agtattagc aacaacctac actggtatca acaaaaatca   120
catgagtctc caaggcttct catcaagtat gcttcccagt ccatctctgg gatcccctcc   180
aggttcagtg gtagtggatc aggacagat tcactctca gtatcaacag tgtggagact    240
gaagattttg gaatgtattt ctgtcaacag agtaacagct ggccgctcac gttcggtgct   300
gggaccaagc tggagctgaa t                                            321

<210> SEQ ID NO 26
<211> LENGTH: 107
<212> TYPE: PRT
<213> ORGANISM: Artificial
<220> FEATURE:
<223> OTHER INFORMATION: Light chain variable region amino acid sequence
      of mAb1-15

<400> SEQUENCE: 26

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Leu
            85                  90                  95

Thr Phe Gly Ala Gly Thr Lys Leu Glu Leu Asn
            100                 105

<210> SEQ ID NO 27
<211> LENGTH: 351
<212> TYPE: DNA
<213> ORGANISM: Artificial
<220> FEATURE:

<223> OTHER INFORMATION: Heavy chain variable region nucleotide sequence of mAb1-25

<400> SEQUENCE: 27

```
gaagtgaagc tggtggagtc tgggggagac ttagtgaagc ctggagggtc cctgaaactc      60
tcctgtgtag cctctggatt cgctttcagt agctatgaca tgtcttgggt tcgccaaact     120
ccggagaagc ggctggagtg ggtcgctacc attagtggtg gtggtcgtta cacctactat     180
ccagacactg tgaagggccg attcaccatc tccagagaca tgccaggaa cacccactac      240 ctgcaaatga gcagtctgag gtctgaggac acggccctct attttgtgc aagtccttac      300 ggcggttact tcgatgtctg gggcgcaggg accacggtca ccgtctcctc a              351
```

<210> SEQ ID NO 28
<211> LENGTH: 117
<212> TYPE: PRT
<213> ORGANISM: Artificial
<220> FEATURE:
<223> OTHER INFORMATION: Heavy chain variable region amino acid sequence of mAb1-25

<400> SEQUENCE: 28

```
Glu Val Lys Leu Val Glu Ser Gly Gly Asp Leu Val Lys Pro Gly Gly
1               5                   10                  15

Ser Leu Lys Leu Ser Cys Val Ala Ser Gly Phe Ala Phe Ser Ser Tyr
            20                  25                  30

Asp Met Ser Trp Val Arg Gln Thr Pro Glu Lys Arg Leu Glu Trp Val
        35                  40                  45

Ala Thr Ile Ser Gly Gly Gly Arg Tyr Thr Tyr Tyr Pro Asp Thr Val
    50                  55                  60

Lys Gly Arg Phe Thr Ile Ser Arg Asp Asn Ala Arg Asn Thr His Tyr
65                  70                  75                  80

Leu Gln Met Ser Ser Leu Arg Ser Glu Asp Thr Ala Leu Tyr Phe Cys
                85                  90                  95

Ala Ser Pro Tyr Gly Gly Tyr Phe Asp Val Trp Gly Ala Gly Thr Thr
            100                 105                 110

Val Thr Val Ser Ser
        115
```

<210> SEQ ID NO 29
<211> LENGTH: 321
<212> TYPE: DNA
<213> ORGANISM: Artificial
<220> FEATURE:
<223> OTHER INFORMATION: Light chain variable region nucleotide sequence of mAb1-25

<400> SEQUENCE: 29

```
gatattgtgc taactcagtc tccagccacc ctgtctgtga ctccgggagc tagagtcagt      60
ctttcctgca gggccagtca agtattagc aacttcctac actggtatca acaaaaatca     120
catgagtctc caaggcttct catcaaatat gcttctcagt ccatttctgg gatcccctcc     180
aggttcagtg gcagtggatc aggacagat ttcactctca gtatcagcag tgtggagact      240
gaagattttg gaatgtattt ctgtcaacag agtaacagct ggcctcatac gttcggtgct     300
gggaccaagc tggagctgaa a                                                321
```

<210> SEQ ID NO 30
<211> LENGTH: 107
<212> TYPE: PRT

<213> ORGANISM: Artificial
<220> FEATURE:
<223> OTHER INFORMATION: Light chain variable region amino acid sequence of mAb1-25

<400> SEQUENCE: 30

```
Asp Ile Val Leu Thr Gln Ser Pro Ala Thr Leu Ser Val Thr Pro Gly
1               5                   10                  15

Ala Arg Val Ser Leu Ser Cys Arg Ala Ser Gln Ser Ile Ser Asn Phe
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Ser Ser Val Glu Thr
65                  70                  75                  80

Glu Asp Phe Gly Met Tyr Phe Cys Gln Gln Ser Asn Ser Trp Pro His
                85                  90                  95

Thr Phe Gly Ala Gly Thr Lys Leu Glu Leu Lys
            100                 105
```

<210> SEQ ID NO 31
<211> LENGTH: 354
<212> TYPE: DNA
<213> ORGANISM: Artificial
<220> FEATURE:
<223> OTHER INFORMATION: Heavy chain variable region nucleotide sequence of mAb1-15-humanized

<400> SEQUENCE: 31

```
gaggtgcagc tggtggagag cggcggcggc ctggtgcagc ccggcggcag cctgaggctg    60
agctgcgccg ccagcggctt caccttcagc agctacgaca tgagctgggt gaggcaggcc   120
cccggcaaga ggctggagtg ggtggccacc atcagcggcg gcggcaggta cacctactac   180
cccgacagcg tgaagggcag gttcaccatc agcagggaca acgccaagaa cagcctgtac   240
ctgcagatga acagcctgag ggccgaggac accgccgtgt actactgcgc caacaggtac   300
gacgtggact ggttcgccta ctggggccag ggcaccctgg tgaccgtgag cagc          354
```

<210> SEQ ID NO 32
<211> LENGTH: 321
<212> TYPE: DNA
<213> ORGANISM: Artificial
<220> FEATURE:
<223> OTHER INFORMATION: Light chain variable region nucleotide sequence of mAb1-15-humanized

<400> SEQUENCE: 32

```
gagatcgtgc tgacccagag ccccgccacc ctgagcctga gccccggcga gagggccacc    60
ctgagctgca gggccagcca gagcatcagc aacaacctgc actggtacca gcagaagccc   120
ggccaggccc ccaggctgct gatcaagtac gccagccaga gcatcagcgg catccccgcc   180
aggttcagcg gcagcggcag cggcaccgac ttcaccctga ccatcagcag cctggagccc   240
gaggacttcg ccgtgtactt ctgccagcag agcaacagct ggcccctgac cttcggccag   300
ggcaccaagg tggagatcaa g                                              321
```

<210> SEQ ID NO 33
<211> LENGTH: 351
<212> TYPE: DNA
<213> ORGANISM: Artificial

<220> FEATURE:
<223> OTHER INFORMATION: Heavy chain variable region nucleotide sequence of mAb1-25-Humanized

<400> SEQUENCE: 33

```
gaagtcaaac tcgtggagtc cggcggaggc ctcgttcaac caggtggatc tcttcgtttg    60
tcctgcgcag catcaggatt cgctttctcc agctacgaca tgagctgggt ccgacaggct   120
cctggaaaga ggctgaatgg ggttgctact atcagcggcg gtggtagata tacttattac   180
cccgataccg taaaggggag gttcaccatt agtcgcgata cgccaaaaa ttcacactac    240
ctgcagatga actctctgcg ggccgaggac accgccgtgt acttttgtgc cagtccctat   300
ggcgggtatt ttgacgtgtg gggccagggg acactggtga ctgtgagttc t            351
```

<210> SEQ ID NO 34
<211> LENGTH: 321
<212> TYPE: DNA
<213> ORGANISM: Artificial
<220> FEATURE:
<223> OTHER INFORMATION: Light chain variable region nucleotide sequence of mAb1-25-Humanized

<400> SEQUENCE: 34

```
gagatcgtcc ttacccaatc accagcaacc ttgtcactgt caccaggtga agagcaacc    60
ctcagttgta gggctagtca gagtatctcc aacttcctgc actggtacca gcagaagcct   120
ggacaggccc ctcggttgct cattaagtac gcctctcaat ctatcagcgg aatcccgct   180
cgcttttctg gctctggctc cgggactgat ttcactctga caatttccag cctggaaccc   240
gaggactttg ccgtttattt ttgccagcag agcaatagct ggccccatac attcgggcag   300
ggcacaaaag tggagataaa a                                             321
```

<210> SEQ ID NO 35
<211> LENGTH: 981
<212> TYPE: DNA
<213> ORGANISM: Artificial
<220> FEATURE:
<223> OTHER INFORMATION: Nucleotide sequence of human immunoglobulin IgG4 constant region

<400> SEQUENCE: 35

```
gcaagtacca agggacctag tgttttccct cttgcacctt gctccaggtc aacatcagag    60
tccacagctg ctcttggatg tctcgttaag gactacttcc cagagccagt taccgtatcc   120
tggaactccg gagctttgac aagcggcgtt catacattcc cagctgtgtt gcagagttct   180
gggttgtaca gtttgagctc agtggtgacc gtgccttcat cttctttggg cactaagacc   240
tacacctgca acgtggatca caagccaagc aacaccaagg tggataagag ggtggagtcc   300
aagtacggcc caccatgtcc tccatgtcca gcccctgaat ttttgggcgg gccttctgtc   360
tttctgtttc ctcctaaacc taaagatacc ctgatgatca gccgcacacc cgaagtcact   420
tgtgtggtcg tggatgtgtc tcaggaagat cccgaagtgc agtttaactg gtatgtcgat   480
ggcgtggaag tgcataatgc caaaactaag ccccgcgaag aacagttcaa cagcacttat   540
cgggtcgtgt ctgtgctcac agtcctccat caggattggc tgaatgggaa agaatataag   600
tgcaaggtga gcaataaggg cctcccccagc agcatcgaga agactattag caaagccaaa   660
gggcagccac gggaacccca ggtgtacact ctgccccct tcaggagga gatgactaaa    720
aatcaggtct ctctgacttg tctggtgaaa gggttttatc ccagcgacat tgccgtggag   780
tgggagtcta atggccagcc cgagaataat tataagacaa ctccccccgt cctggactct   840
```

```
gacggcagct tttcctgta ttctcggctg acagtggaca aaagtcgctg gcaggagggc    900
aatgtcttta gttgcagtgt catgcatgag gccctgcaca atcactatac acagaaaagc    960
ctgtctctga gtctgggcaa a                                              981
```

<210> SEQ ID NO 36
<211> LENGTH: 327
<212> TYPE: PRT
<213> ORGANISM: Artificial
<220> FEATURE:
<223> OTHER INFORMATION: Amino acid sequence of human immunoglobulin
      IgG4 constant region

<400> SEQUENCE: 36

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
```

<210> SEQ ID NO 37
<211> LENGTH: 1335
<212> TYPE: DNA
<213> ORGANISM: Artificial
<220> FEATURE:
<223> OTHER INFORMATION: Heavy chain full length nucleotide sequence of mAb1-15-Humanized

<400> SEQUENCE: 37

```
gaggtgcagc tggtggagag cggcggcggc ctggtgcagc ccggcggcag cctgaggctg      60
agctgcgccg ccagcggctt caccttcagc agctacgaca tgagctgggt gaggcaggcc     120
cccggcaaga ggctggagtg ggtggccacc atcagcggcg gcggcaggta cacctactac     180
cccgacagcg tgaagggcag gttcaccatc agcagggaca cgccaagaa cagcctgtac      240
ctgcagatga acagcctgag ggccgaggac accgccgtgt actactgcgc caacaggtac     300
gacgtggact ggttcgccta ctggggccag ggcaccctgg tgaccgtgag cagcgcaagt     360
accaagggac ctagtgtttt ccctcttgca ccttgctcca ggtcaacatc agagtccaca     420
gctgctcttg gatgtctcgt taaggactac ttcccagagc cagttaccgt atcctggaac     480
tccggagctt tgacaagcgg cgttcataca ttcccagctg tgttgcagag ttctggggttg    540
tacagtttga gctcagtggt gaccgtgcct tcatcttctt gggcactaa gacctacacc     600
tgcaacgtgg atcacaagcc aagcaacacc aaggtggata gagggtgga gtccaagtac     660
ggcccaccat gtcctccatg tccagcccct gaatttttgg gcgggccttc tgtctttctg     720
tttcctccta aacctaaaga taccctgatg atcagccgca cacccgaagt cacttgtgtg     780
gtcgtggatg tgtctcagga agatcccgaa gtgcagttta ctggtatgt cgatggcgtg     840
gaagtgcata atgccaaaac taagccccgc gaagaacagt tcaacagcac ttatcgggtc     900
gtgtctgtgc tcacagtcct ccatcaggat tggctgaatg ggaaagaata taagtgcaag     960
gtgagcaata agggcctccc cagcagcatc gagaagacta ttagcaaagc caagggcag    1020
ccacgggaac cccaggtgta cactctgccc ccctctcagg aggagatgac taaaaatcag    1080
gtctctctga cttgtctggt gaaagggttt tatcccagcg acattgccgt ggagtgggag    1140
tctaatggcc agcccgagaa taattataag acaactcccc ccgtcctgga ctctgacggc    1200
agcttttcc tgtattctcg gctgacagtg gacaaaagtc gctggcagga gggcaatgtc    1260
tttagttgca gtgtcatgca tgaggccctg cacaatcact atacacagaa aagcctgtct    1320
ctgagtctgg gcaaa                                                    1335
```

<210> SEQ ID NO 38
<211> LENGTH: 321
<212> TYPE: DNA
<213> ORGANISM: Artificial
<220> FEATURE:
<223> OTHER INFORMATION: Nucleotide sequence of human immunoglobulin Kappa chain constant region

<400> SEQUENCE: 38

```
cgcactgtgg ctgccccag tgttttcata tttcccccca gtgatgagca actgaagtcc      60
ggcacagcct ctgttgtatg tctgctgaat aattttatc cacgggaggc caaggtgcag     120
tggaaggtgg acaatgccct gcagtctggg aactctcaag agagtgtgac agagcaggac     180
agtaaagaca gcacctatag cctcagcagc accctgaccc tgtctaaagc cgactatgaa     240
aaacacaaag tgtatgcctg cgaagtgacc catcaggggc tcagctctcc cgttaccaag     300
```

-continued

```
agctttaacc gaggcgaatg t                                              321
```

<210> SEQ ID NO 39
<211> LENGTH: 107
<212> TYPE: PRT
<213> ORGANISM: Artificial
<220> FEATURE:
<223> OTHER INFORMATION: Amino acid sequence of human immunoglobulin
      Kappa chain constant region

<400> SEQUENCE: 39

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 40
<211> LENGTH: 642
<212> TYPE: DNA
<213> ORGANISM: Artificial
<220> FEATURE:
<223> OTHER INFORMATION: Light chain full length nucleotide sequence of
      mAb1-15-Humanized

<400> SEQUENCE: 40

```
gagatcgtgc tgacccagag ccccgccacc ctgagcctga gccccggcga gagggccacc    60
ctgagctgca gggccagcca gagcatcagc aacaacctgc actggtacca gcagaagccc   120
ggccaggccc ccaggctgct gatcaagtac gccagccaga gcatcagcgg catccccgcc   180
aggttcagcg gcagcggcag cggcaccgac ttcaccctga ccatcagcag cctggagccc   240
gaggacttcg ccgtgtactt ctgccagcag agcaacagct ggcccctgac cttcggccag   300
ggcaccaagg tggagatcaa gcgcactgtg gctgccccca gtgttttcat atttccccc    360 agtgatgagc aactgaagtc cggcacagcc tctgttgtat gtctgctgaa taatttttat   420
ccacgggagg ccaaggtgca gtggaaggtg gacaatgccc tgcagtctgg gaactctcaa   480
gagagtgtga cagagcagga cagtaaagac agcacctata gcctcagcag caccctgacc   540
ctgtctaaag ccgactatga aaaacacaaa gtgtatgcct gcgaagtgac ccatcagggg   600
ctcagctctc ccgttaccaa gagctttaac cgaggcgaat gt                      642
```

ANTI-PD-1 MONOCLONAL ANTIBODY, AND PREPARATION METHOD THEREFOR AND APPLICATION THEREOF

FIELD OF THE INVENTION

The present invention relates to the field of biomedicine, in particular to an anti-PD-1 monoclonal antibody, and a preparation method therefor and an application thereof.

BACKGROUND OF THE INVENTION

Human programmed cell death receptor-1 (PD-1) is a type I membrane protein of 288 amino acids and is one of the known major immune checkpoints (Blank et al, 2005, Cancer Immunotherapy, 54:307-314). PD-1 is expressed on activated T lymphocytes, and it binds to the ligands PD-L1 (programmed cell death-Ligand 1) and PD-L2 (programmed cell death-Ligand 2) to inhibit the activity of T lymphocytes and related cellular immune responses in vivo. PD-L2 is mainly expressed on macrophages and dendritic cells, while PD-L1 is widely expressed on B, T lymphocytes and peripheral cells such as microvascular epithelial cells, tissue cells of lung, liver, heart and the like. Numerous studies have shown that the interaction between PD-1 and PD-L1 is not only necessary to maintain the balance of the immune system in vivo, but also the main mechanism and cause of PD-L1 expression-positive tumor cells to evade immune surveillance. By blocking the negative regulation of cancer cells on the PD-1/PD-L1 signaling pathway and activating the immune system, T cell-related tumor-specific cellular immune responses can be promoted, thereby opening a new door for tumor treatment—tumor immunotherapy.

PD-1 (encoded by the gene Pdcd1) is a member of the immunoglobulin superfamily related to CD28 and CTLA-4. Studies have shown that PD-1 negatively regulates antigen receptor signaling upon engagement of its ligands (PD-L1 and/or PD-L2). The structure of murine PD-1 and the co-crystal structure of mouse PD-1 with human PD-L1 have been solved (Zhang, X. et al., Immunity 20: 337-347(2004); Lin et al., Proc. Natl. Acad. Sci. USA 105: 3011-6(2008)). PD-1 and like family members are type I transmembrane glycoproteins containing an Ig variable (V-type) domain responsible for ligand binding and a cytoplasmic tail that is responsible for the binding of signaling molecule. The cytoplasmic tail of PD-1 contains two tyrosine-based signaling motifs, an ITIM (immunoreceptor tyrosine-based inhibition motif) and an ITSM (immunoreceptor tyrosine-based switch motif).

PD-1 plays an important role in tumor immune evasion mechanism. Tumor immunotherapy, which uses the body's own immune system to fight cancer, is a breakthrough in cancer treatment. However, the tumor microenvironment may protect tumor cells from effective immune damage, so how to break the tumor microenvironment becomes the focus of anti-tumor research. Existing research results have identified the role of PD-1 in the tumor microenvironment: PD-L1 is expressed in many mouse and human tumors (and may be induced by IFNγ in most PD-L1-negative tumor cell lines), and presumed to be an important target for mediating tumor immune evasion (Iwai Y. et al., Proc. Natl. Acad. Sci. U.S.A. 99: 12293-12297(2002); Strome S. E. et al., Cancer Res., 63: 6501-6505(2003). In humans, expression of PD-1 (on tumor infiltrating lymphocytes) and/or PD-L1 on tumor cells has been found in a number of primary tumor biopsies assessed by immunohistochemistry. Such tissues include lung cancer, liver cancer, ovarian cancer, cervical cancer, skin cancer, colon cancer, glioma, bladder cancer, breast cancer, kidney cancer, esophageal cancer, gastric cancer, oral squamous cell carcinoma, urothelial cell carcinoma, and pancreatic cancer as well as tumors of the head and neck, and so on. Thus, blockade of the PD-1/PD-L1 interaction could enhance tumor-specific T-cell immunity activity and is helpful in clearance of tumor cells by the immune system. Therefore, PD-1 has become a hot target for the development of tumor immunotherapy drugs.

However, existing anti-PD-1 monoclonal antibodies have defects of weak selectivity and low affinity. Therefore, the development of a novel anti-PD-1 monoclonal antibody and its application to the preparation of related drugs for treating tumors and treating autoimmune diseases has become a technical problem to be solved.

SUMMARY OF THE INVENTION

The technical problem to be solved by the present invention is to overcome the defects of weak selectivity and low affinity of current anti-human PD-1 monoclonal antibodies, and provide a novel anti-human PD-1 monoclonal antibody, and also provide a preparation method and application of the monoclonal antibody, thereby completing the present invention.

Thus, a first object of the present invention is to provide an anti-human PD-1 monoclonal antibody.

A second object of the present invention is to provide a nucleotide molecule encoding the anti-human PD-1 monoclonal antibody.

A third object of the present invention is to provide an expression vector comprising the nucleotide molecule.

A fourth object of the present invention is to provide a host cell comprising the expression vector.

A fifth object of the present invention is to provide a method for the preparation of the anti-human PD-1 monoclonal antibody.

A sixth object of the present invention is to provide a composition comprising the anti-human PD-1 monoclonal antibody.

A seventh object of the present invention is to provide the use of the anti-human PD-1 monoclonal antibody for preparing drugs.

In order to achieve the above objects, the present invention provides the following technical solutions:

The first technical solution provided by the present invention is to provide an anti-human PD-1 monoclonal antibody, which comprises:

(1) a heavy chain complementarity determining region CDRH1, CDRH2, CDRH3, wherein the CDRH1 having the amino acid sequence as shown in SEQ ID NO: 1 or SEQ ID NO: 13, the CDRH2 having the amino acid sequence as shown in SEQ ID NO: 2 or SEQ ID NO: 14, and the CDRH3 having the amino acid sequence as shown in SEQ ID NO: 3 or SEQ ID NO: 15, and (2) a light chain complementarity determining region CDRL1, CDRL2, CDRL3, wherein the CDRL1 having the amino acid sequence as shown in SEQ ID NO: 4 or SEQ ID NO: 16, the CDRL2 having the amino acid sequence as shown in SEQ ID NO: 5 or SEQ ID NO: 17, and the CDRL3 having the amino acid sequence as shown in SEQ ID NO: 6 or SEQ ID NO: 18.

In the art, the binding regions of an antibody typically comprise a light chain variable region and a heavy chain variable region, and each variable region comprises three domains, CDR1, CDR2 and CDR3. The single-chain antibody of the present invention is a conventional single-chain antibody, which comprises a heavy chain variable region, a light chain variable region and a short peptide of 15 to 20 amino acids. Preferably, the anti-human PD-1 monoclonal antibody of the present invention comprises a heavy chain variable region having the amino acid sequence as shown in SEQ ID NO: 7 or SEQ ID NO: 19 or SEQ ID NO: 24 or SEQ ID NO: 28, and a light chain variable region having the amino acid sequence as shown in SEQ ID NO: 9 or SEQ ID NO: 21 or SEQ ID NO: 26 or SEQ ID NO: 30. More preferably, the anti-human PD-1 monoclonal antibody of the present invention comprises a heavy chain having the amino acid sequence as shown in SEQ ID NO: 8 or SEQ ID NO: 20, and a light chain having the amino acid sequence as shown in SEQ ID NO: 10 or SEQ ID NO: 22.

The monoclonal antibody of the present invention can be prepared by conventional techniques in the art, including hybridoma technology, phage display technology, single lymphocyte gene cloning technology, etc., and preferably, the monoclonal antibody is prepared from wild-type or transgenic mice by hybridoma technology.

The second technical solution provided by the present invention is: a nucleotide molecule, which encodes the anti-human PD-1 monoclonal antibody as described above.

Wherein the nucleotide molecule has a nucleotide sequence encoding the heavy chain variable region of the anti-human PD-1 monoclonal antibody as shown in SEQ ID NO: 23 or SEQ ID NO: 27 or SEQ ID NO: 31 or SEQ ID NO: 33, and a nucleotide sequence encoding the light chain variable region as shown in SEQ ID NO: 25 or SEQ ID NO: 29 or SEQ ID NO: 32 or SEQ ID NO: 34.

Wherein the nucleotide molecule has a nucleotide sequence encoding the heavy chain of the anti-human PD-1 monoclonal antibody preferably as shown in SEQ ID NO: 11, and a nucleotide sequence encoding the light chain preferably as shown in SEQ ID NO: 12, or the nucleotide molecule has a nucleotide sequence encoding the heavy chain of the anti-human PD-1 monoclonal antibody as shown in SEQ ID NO: 37, and a nucleotide sequence encoding the light chain as shown in SEQ ID NO: 40.

The preparation method of the nucleotide molecule of the present invention is a conventional preparation method in the art, and preferably includes the following preparation methods: a nucleotide molecule encoding the above monoclonal antibody is obtained by a gene cloning technique, such as a PCR method, or a nucleotide molecule encoding the above monoclonal antibody is obtained by artificial synthesis of complete sequence.

It is known to those skilled in the art that the nucleotide sequence encoding the amino acid sequence of the above monoclonal antibody may be appropriately introduced with a substitution, deletion, alteration, insertion or addition to provide a homologue of a polynucleotide. The homologue of a polynucleotide of the present invention can be prepared by substitution, deletion, or addition of one or more bases encoding the monoclonal antibody gene within the range of maintaining the antibody activity.

The third technical solution provided by the present invention is: an expression vector, which comprises the nucleotide molecule as described above.

Wherein the expression vector is a conventional expression vector in the art, which refers to an expression vector comprising an appropriate regulatory sequence, such as a promoter sequence, a terminator sequence, a polyadenylation sequence, an enhancer sequence, a marker gene and/or sequence, and other appropriate sequences. The expression vector can be a virus or a plasmid, such as a suitable phage or phagemid, for more technical details, refer to, for example, Sambrook et al., Molecular Cloning: A Laboratory Manual, 2nd Edition, Cold Spring Harbor Laboratory Press, 1989. Refer to Current Protocols in Molecular Biology, 2nd Edition, edited by Ausubel et al. for many known techniques and protocols for nucleic acid manipulation.

The expression vector of the present invention is preferably pDR1, pcDNA3.1, pDHFR, pCG-53 or pCHO 1.0, and more preferably pCHO 1.0.

The fourth technical solution provided by the present invention is a host cell, which comprises the expression vector as described above.

The host cell of the present invention is a variety of conventional host cells in the art, as long as it enables the above recombinant expression vector to stably replicate on its own, and the nucleotides carried thereby can be efficiently expressed. Wherein the host cell comprises a prokaryotic expression cell and a eukaryotic expression cell, the expression vector preferably comprises: COS, CHO (Chinese Hamster Ovary), NS0, sf9, sf21, DH5α, BL21 (DE3) or TG1, and more preferably is E. coli TG1, BL21 (DE3) cell (expressing single-chain antibody or Fab antibody) or CHO-K1 cell (expressing full-length IgG antibody). A preferred recombinant expression transformant of the present invention can be obtained by transforming the aforementioned expression vector into a host cell. The transformation method is a conventional transformation method in the art, and preferably a chemical transformation method, a heat shock method or an electro-transformation method.

The fifth technical solution provided by the present invention is: a method for preparing the anti-human PD-1 monoclonal antibody described above, which comprises the following steps:

a) under expression conditions, cultivating the host cell of the present invention to express the anti-human PD-1 monoclonal antibody;

b) isolating and purifying the anti-human PD-1 monoclonal antibody of step a).

The method for culturing the host cell of the present invention, and the method for isolating and purifying the anti-human PD-1 monoclonal antibody are conventional methods in the art, and for the specific operation method, refer to the corresponding cell culture technical handbook and monoclonal antibody isolation and purification technical handbook. The preparation method of the anti-human PD-1 monoclonal antibody disclosed in the present invention comprises: cultivating the host cell described above under expression conditions to express an anti-human PD-1 monoclonal antibody; isolating and purifying the anti-human PD-1 monoclonal antibody. By the methods described above, the recombinant protein can be purified to a substantially homogeneous material, such as being a single band on SDS-PAGE electrophoresis.

The anti-human PD-1 monoclonal antibody disclosed in the present invention can be isolated and purified by affinity chromatography, and can be eluted by a conventional method, such as high salt buffer, pH change, etc., depending on the characteristics of the used affinity column. The inventors of the present invention have conducted a detection experiment on the obtained anti-human PD-1 monoclonal antibody, and the experimental results show that the monoclonal antibody can bind well to human PD-1 and has a high affinity.

A sixth technical solution provided by the present invention is: a composition, which comprises the anti-human PD-1 monoclonal antibody described above and a pharmaceutically acceptable carrier.

The anti-human PD-1 monoclonal antibody provided by the present invention can be combined with a pharmaceutically acceptable carrier to form a pharmaceutical preparation composition which exerts a therapeutic effect more stably, and these preparations can ensure that the amino acid core sequence of the anti-human PD-1 monoclonal antibody of the present invention has an integrity conformation, and protect multifunctional groups of the protein from degradation (including but not limited to coagulation, deamination or oxidation). Typically, for the liquid preparation, it is stable for at least one year at 2° C. to 8° C., and for the lyophilized preparation, it is stable for at least six months at 30° C. The anti-human PD-1 monoclonal antibody preparation may be a preparation commonly used in the pharmaceutical field such as suspension, water needle, or lyophilized preparation, and preferably water needle or lyophilized preparation.

For the water-needle or lyophilized preparation of the anti-human PD-1 monoclonal antibody of the present invention, pharmaceutically acceptable carriers include, but not limited to, surfactants, solution stabilizers, isotonicity adjusting agents, buffers or a combination thereof. The surfactants preferably include but not limited to, nonionic surfactants such as polyoxyethylene sorbitan fatty acid ester (Tween 20 or 80); poloxamer (e.g. poloxamer 188); Triton; sodium dodecyl sulfate (SDS), sodium lauryl sulfate; tetradecyl, linoleyl or octadecylsarcosine; Pluronics; MONAQUAT™, etc. And the surfactants are added in an amount such that the granulation tendency of the anti-human PD-1 monoclonal antibody is minimized. The solution stabilizers preferably include but not limited to, one of the following: sugars, for example, reducing sugars and non-reducing sugars; amino acids, for example, monosodium glutamate or histidine; alcohols, for example, triols, higher sugar alcohols, propylene glycol, polyethylene glycol and the like, or a combination thereof. The solution stabilizer should be added in an amount such that the final formed preparation remains stable for a period of time that is considered stable by those skilled in the art. Isotonicity adjusting agents preferably include but not limited to, one of sodium chloride, mannitol, or a combination thereof. The buffers preferably include but not limited to, one of Tris, histidine buffer, phosphate buffer, or a combination thereof.

The seventh technical solution provided by the present invention is: the use of the anti-human PD-1 monoclonal antibody of the present invention or a composition thereof for preparing drugs.

The drugs according to the invention are preferably drugs for treating tumors, treating autoimmune diseases, treating infectious diseases and/or inhibiting graft rejection, and more preferably anti-tumor drugs, drugs for treating autoimmune diseases, and preferably anti-tumor drugs. The anti-human PD-1 monoclonal antibody of the present invention may be used alone or in combination with an anti-PD-L1 monoclonal antibody or other anti-tumor drugs.

The tumors against which the anti-tumor drugs are targeted preferably include but not limited to, one or more of lung cancer, liver cancer, ovarian cancer, cervical cancer, skin cancer, colon cancer, glioma, bladder cancer, breast cancer, kidney cancer, esophageal cancer, gastric cancer, oral squamous cell carcinoma, urothelial cell carcinoma, pancreatic cancer, and/or head and neck tumor. Preferably, the tumor is colorectal cancer.

The anti-tumor drugs of the present invention refers to a drug that inhibits and/or treats a tumor, which may include the delay in the development of symptoms associated with tumors and/or the reduction in the severity of these symptoms, and further includes the alleviation of symptoms associated with the tumors and the prevention of the other symptoms, as well as the reduction or prevention of metastasis of the tumors.

When the anti-human PD-1 monoclonal antibody and the composition thereof in the present invention are administered to animals including human, the dose varies depending on the age and weight of the patient, the characteristics and severity of the disease, and the administration route, which can refer to the results of the animal experiment and various conditions. The total dose cannot exceed a certain range. Specifically, the dose for intravenous injection is 1-1800 mg/day.

Based on the common knowledge in the art, the above various preferred conditions can be arbitrarily combined to obtain each of the preferred embodiments of the present invention.

The reagents and raw materials used in the present invention are commercially available.

The beneficial effects of the present invention are that: the anti-human PD-1 monoclonal antibody provided by the invention has good biological activity, can effectively bind to the extracellular region of the human PD-1 protein receptor, and can effectively block the PD-1 protein at the protein level and the cellular level, and prevent the binding of PD-1 protein to ligand PD-L1. The monoclonal antibody can be used alone or in combination with other anti-tumor drugs in the diagnosis and screening of tumor immunotherapy and PD-L1 positive tumor patients, that is, can be effectively used for preparing dugs for treating tumors, infectious diseases, autoimmune diseases and anti-immune rejection, and the like.

DETAILED DESCRIPTION OF THE INVENTION

Figure 1:
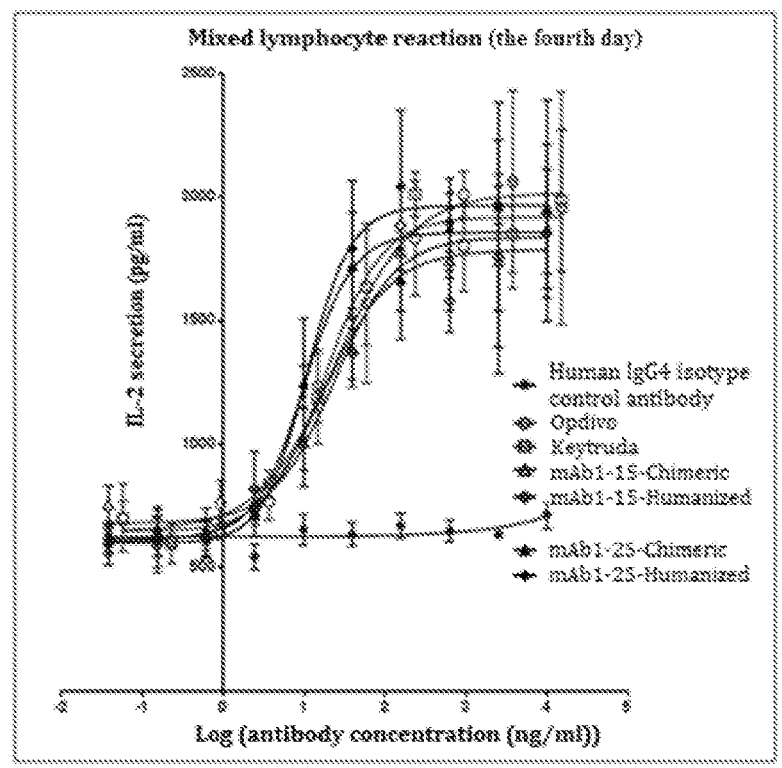
FIG. 1: Stimulation of IL-2 secretion in MLR by the PD-1 antibody.

The invention is further illustrated by the following examples, but the invention is not intended to be limited to the scope of the described examples. The experimental methods in the following examples which do not specify the specific conditions are selected according to conventional methods and conditions, or according to the product specifications. The room temperature described in the examples is conventional room temperature in the art, generally 10 to 30° C.

The experimental materials and their sources used in the following examples and the preparation methods of the experimental reagents are specifically described below.

Experimental Materials:

Human whole blood: provided by Shanghai Changhai Hospital; human peripheral blood mononuclear cells (PBMC) were isolated from human whole blood by Ficoll density centrifugation; human CD14+ monocytes and CD4+ T cells were isolated using a magnetic cell sorting system from Miltenyi Biotec; the above cells were routinely cultured in AIM-V medium in a 37° C., 5% $CO_2$ cell culture incubator.

Others: Histopaque-1077, sigma; CD4 MicroBeads, MiltenyiBiotec; OctoMACS Starting Kit (cell sorting kit), MiltenyiBiotec; MS MACS sorting column, MiltenyiBiotec; Recombinant human granulocyte macrophage colony stimulating factor for injection (GM-CSF), Xiamen Tebao Biological Engineering Co., Ltd., formulated into 100 µg/ml mother liquor and then stored in a refrigerator at −80° C.; recombinant human IL-4, R&D Systems, formulated into 100 µg/ml mother liquor and then stored in a refrigerator at −80° C.; AIM-V, Gibco; streptavidin-HRP, BD Pharmingen; anti-human IL-2 antibody, BD Pharmingen; biotinylated anti-human IL-2 antibody, BD Pharmingen; anti-human IFN-gamma antibody, BD Pharmingen; biotinylated anti-human IFN-gamma antibody, BD Pharmingen; human IFN-gamma standard sample, BD Pharmingen; human IL-2 standard sample, purchased from Beijing Shuanglu Pharmaceutical Co., Ltd., injectable pharmaceutical grade, formulated into a high-concentration mother liquor and then stored in a refrigerator at −80° C.; Cell Titer-Glo® luminescent cell viability assay kit, Promega.

Experimental Reagents:

ELISA coating solution: sodium carbonate 1.59 g, sodium hydrogen carbonate 2.93 g, made up to 1000 ml with purified water of pH 7.0.

PBST: potassium dihydrogen phosphate 0.2 g, disodium hydrogen phosphate dodecahydrate 2.9 g, sodium chloride 8.0 g, potassium chloride 0.2 g, Tween-20 1 ml, made up to 1000 ml with purified water of pH 7.0.

ELISA chromogenic solution A: sodium acetate 13.6 g, citric acid 1.6 g, 30% hydrogen peroxide 0.3 ml, made up to 500 ml with purified water of pH 7.0.

ELISA chromogenic solution B: ethylenediaminetetraacetic acid disodium 0.2 g, citric acid 0.95 g, glycerol 50 ml, TMB 0.15 g dissolved in 3 ml DMSO, made up to 500 ml with purified water of pH 7.0.

ELISA stop solution: 98% concentrated sulfuric acid 111 ml, made up to 1000 ml with purified water of pH 7.0.

Example 1. Preparation of Human PD-1 and its Ligand PD-L1

The cDNA of human PD-1 was purchased from Origene (Cat. No. SC117011). The primers were designed, and the coding region of the extracellular domain was amplified using the cDNA of the PD-1 gene as the template, and the Fc coding region was amplified using the cDNA of the human IgG1 gene as the template; the above amplified PCR fragments were recovered, and the above fragments were recombined by Overlap PCR. When the primers were designed, the signal peptide (MGVKVLFALICIAVAEA)-coding region was introduced at the 5-end, and the corresponding restriction sites were introduced at both ends; the pCHO1.0 vector and the aforementioned recombinant PCR fragment were digested with Avr II and Pac I; the digested products were purified, ligated, and transformed into TOP10 competent cells, and applied on the LB (Amp) plate medium overnight for culturing; the colonies were picked, cultured and amplified, and then the plasmid was extracted. The plasmid was digested with Avr II and Pac I to identify whether or not the gene fragment was inserted; positive plasmids were sequenced. The clones having completely correct sequences were selected for CHO cell transfection. The cDNA of ligand PD-L1 of PD-1 was purchased from Sino Biological Inc., product code HG10084-M. A fusion gene expression vector of the extracellular domain of PD-L1 and the Fc fragment of human antibody was constructed in the same manner as described above.

The above pCHO 1.0 (human PD-1-hFc and PD-L1-hFc) vectors were transfected into CHO—S cell line (purchased from Life Technologies) by liposome method, respectively, cultured in a CD FortiCHO medium containing 6 mM glutamine (purchased from Gibco) for 2 days and then positive cell clones were screened using puromycin (purchased from Gene Operation) and methotrexate (purchased from Sigma). Positive clones were inoculated into shake flasks, 200 ml per vial, at a density of $3 \times 10^5$ cells/ml, and the medium was a CD FortiCHO medium containing 6 mM glutamine and 1/100 by volume of anti-aggregation reagent (purchased from Invitrogen). After 12 days of culture, the supernatant was collected, and the PD-1-hFc antigen and PD-L1-hFc were purified using a Protein A affinity chromatography column. Protein quantification was carried out by bicinchoninic acid (BCA) method. The purified proteins were used for the following mouse immunization and further analysis and research.

Example 2. Immunization of Mice with Human PD-1-hFc as Antigen and Preparation and Screening of Hybridomas The human PD-1-hFc antigen prepared in Example 1 was diluted with normal saline to 50 µg/75 µl, mixed with an equal volume of Freund's complete adjuvant (purchased from Sigma), fully phaco-emulsified, and then administrated to 4-5 weeks old Balb/c mice (purchased from Shanghai Lingchang Biotechnology Co., Ltd., animal production license number: SCXK (Shanghai) 2013-0018) by multi-point subcutaneous injection. Three weeks later, the PD-1-hFc antigen was diluted to 50 µg/75 µl with normal saline and mixed with an equal volume of Freund's incomplete adjuvant (purchased from Sigma), fully phaco-emulsified, and then administrated to mice by multipoint subcutaneous immunization. Such immunization was repeated two weeks later. On the seventh day after the third immunization, one drop of blood was collected from all mice to separate serum, and serum titer was detected by ELISA.

Titer was determined by ELISA: Human PD-1-hFc antigen was used for coating the ELISA plate at a concentration of 2.5 µg/ml, 100 µl for each well, overnight at 4° C. The plate was washed twice with PBST (PBS containing 0.5% Tween-20) and patted dry. Each well was added with 200 µl of coating buffer containing 1% BSA, blocked at room temperature for 4 hours and patted dry, and stored in a refrigerator at −20° C. until use. When detection was performed, various concentrations of mouse serum were added to the ELISA plate with 100 µl per well. Two replicate wells were set up, and incubated at room temperature for 1.5 hours. The plate was washed 3 times with PBST and then patted dry. 100 µl of HRP-labeled goat anti-mouse Ig antibody (purchased from Sigma) diluted 1:10000 with PBST was added, and incubated for 1 hour at room temperature. The plate was washed 3 times with PBST and then patted dry. Each well was added with 100 µl of chromogenic solution (chromogenic solution A and chromogenic solution B of ELISA were mixed at a volume ratio of 1:1 before use) to develop color and then each well was added with 100 µl of 2M $H_2SO_4$ as stop solution to terminate the reaction. The OD value of each well was measured immediately at a wavelength of 450 nm using a microplate reader (Molecular Device). For the mice with serum antibody titers >100,000, the following immunization protocol was performed one week after blood collection: 10 μg antigen protein/100 μl normal saline/mouse was injected into the tail vein.

The spleen cells of the mice with serum antibody titers >100,000 were taken for fusion three days after the last immunization. Myeloma sp2/0 cells in good-growth condition (derived from the Cell Bank of the Typical Cell Culture Collection Committee of the Chinese Academy of Sciences) were cultured in a 37° C., 5% $CO_2$ incubator and the medium was renewed one day prior to fusion. The fusion and screening process was as follows: the spleens of the mice were taken and ground, and the B lymphocytes were separated, washed and counted; the two cells were mixed in a ratio of spleen cells: sp2/0 cells=10:1, centrifuged at 1500 rpm for 7 minutes, and the supernatant was discarded; 1 ml of PEG-1450 (purchased from Sigma) was added in 1 minute, gently shaken for 90 seconds, 5 ml of serum-free DMEM (purchased from Gibco) was added in 2.5 minutes, and then 5 ml of serum-free medium was added in one time to terminate the reaction, allowed to stand for 5 minutes and centrifuged at 1280 rpm for 8 minutes. According to a ratio of two million sp2/0 cells per 96-well plate, the cells were uniformly inoculated in a 96-well plate with 200 μl per well, and first screened with HAT medium containing hypoxanthine (H), aminopterin (A) and thymidine (T), and the medium was half-renewed every 3-4 days (half of the old culture solution was aspirated and the same amount of fresh HAT medium was added). After 10 days, when the hybridoma cells were spread over 10% of the bottom of the 96-well plate, the supernatants were taken for ELISA using the plate coated with PD-1-hFc. The ELISA method was the same as described above. Positive hybridoma clones were selected for expansion in 24-well plates and subcloned by limiting dilution. Hybridoma strains stably expressing antibodies of interest were obtained and then cryopreserved.

Example 3. Blocking Effect of PD-1 Binding to PD-L1 by Murine Anti-Human PD-1 Monoclonal Antibodies The stable monoclonal cell line obtained in Example 2 was cultured in serum-free medium Hybridoma-SFM (purchased from Life Technologies) for 7 days, and then the murine anti-human PD-1 monoclonal antibodies were purified from the culture supernatants by Protein G affinity chromatography (purchased from GE). The purified antibodies were subjected to concentration determination. Then ELISA was used to study the blocking effects of PD-1 binding to PD-L1 by murine anti-human PD-1 monoclonal antibodies.

Human PD-1-hFc was used for coating the ELISA plate at a concentration of 2.5 μg/ml, 100 μl for each well, overnight at 4° C. The plate was washed twice with PBST (PBS containing 0.5% Tween-20) and patted dry. Each well was added with 200 μl of coating buffer containing 1% BSA, blocked at room temperature for 4 hours and patted dry, and stored in a refrigerator at −20° C. until use. The above-mentioned PD-1-hFc-coated ELISA plate was simultaneously added with an appropriate concentration of biotinylated PD-L1-hFc (the PD-L1-hFc prepared in Example 1 was biotinylated with EZ-Link™ NHS-Biotin, and the specific steps were operated according to the manufacturer's instructions) and sufficient amounts of murine anti-human PD-1 monoclonal antibodies, incubated for 1 hour at room temperature; washed 3 times with PBST; added with appropriately diluted Streptavidin-HRP, 100 μl per well; washed 3 times with PBST and patted dry; 100 μl of chromogenic solution was added to each well, and then 100 μl of 2M $H_2SO_4$ stop solution was added to each well to terminate the reaction. The OD value of each well was measured at a wavelength of 450 nm using a microplate reader (Molecular Device).

Example 4. Evaluation of Functional Activity of Murine Anti-Human PD-1 Monoclonal Antibodies on Enhancing Mixed Lymphocyte Reaction (MLR)

Peripheral blood mononuclear cells (PBMCs) were isolated from human blood by Histopaque, and then the mononuclear cell subsets in PBMCs were isolated by adherence method, and then the mononuclear cells were induced by IL-4 and GM-CSF to differentiate into induced dendritic cells. After seven days, the above induced dendritic cells were collected by digestion. PBMCs were isolated from the blood of the other donors by the above method, and then CD4 positive T cells were isolated therefrom using MACS magnets and CD4 MicroBeads (purchased from Miltenyi biotec). The induced dendritic cells ($10^4$ cells/well) and the isolated CD4-positive T cells ($10^5$ cells/well) were mixed in proportion and inoculated into a 96-well plate with 150 μl per well; after several hours, 50 μl of murine anti-human PD-1 antibodies serially diluted with AIM-V medium was added to the above 96 well plate; the positive control antibodies Opdivo and Keytruda, which have been approved for marketing, and the unrelated control antibody that did not bind to PD-1 were set simultaneously; the plates were incubated in a 37° C. incubator for 4 days. The secretion of IL-2 and IFN-gamma and the proliferation of lymphocytes were then detected according to standard protocols. Detection of IL-2 and IFN-gamma secretion was performed using the standard double-antibody sandwich method (the paired antibodies for the relevant detection were purchased from BD Biosciences), and the proliferation of lymphocytes was detected by the Cell Titer-Glo® method (the relevant reagents were purchased from Promega). Opdivo was purchased from Bristol-Myers Squibb, LOT was 4M59291, EXP was SEP2016; Keytruda was purchased from Merk, and LOT and EXP were K013835/070C12015. The medium used in this example was AIM-V (purchased from Life Technologies). All data were read using a multi-labeled microplate reader (Molecular Device), data analysis and drawing were performed using GraphPad Prism6, and EC50 was calculated. After the above purified murine anti-human PD-1 monoclonal antibodies were subjected to MLR evaluation, the antibodies that can effectively enhance the MLR intensity were screened and advanced to the next experiment.

Example 5. Determination of Nucleotide and Amino Acid Sequences of Preferred Murine Anti-Human PD-1 Monoclonal Antibodies According to the screening results of Examples 3 and 4, clones No. 1-15 and 1-25 (mAb1-15 and mAb1-25) were finally picked as lead antibodies. Total RNA was extracted from monoclonal hybridoma cell strains corresponding to clones No. 1-15 and 1-25 using Trizol (purchased from Life technologies), and mRNA was reverse transcribed into cDNA using a reverse transcription kit (purchased from Takara). By the primer combinations reported in the literature (Antibody Engineering, Volume 1, Edited by Roland Kontermann and Stefan Dübel; the sequence of the combined primers from page 323), the genes of light chain variable region and heavy chain variable region of the murine anti-human PD-1 monoclonal antibodies were amplified by PCR, and then the PCR products were cloned into the pMD18-T vector, and the variable region gene sequences were sequenced and analyzed.

The sequence information of murine antibody No. 1-15 (mAb1-15) is as follows: the heavy chain variable region gene sequence is 354 bp in length, encoding 118 amino acid residues, the nucleotide sequence is shown in SEQ ID NO: 23, and the amino acid sequence is shown in SEQ ID NO: 24; the light chain variable region gene sequence is 321 bp in length, encoding 107 amino acid residues, the nucleotide sequence is shown in SEQ ID NO: 25, and the amino acid sequence is shown in SEQ ID NO: 26.

SEQ ID NO: 23
GAAGTGAACCTGGTGGAGTCTGGGGGAGGCTTAGTGAAGCCTGGAGGGTC

CCTGAAACTCTCCTGTGCAGCCTCTGGATTCACTTTCAGTAGCTATGACA

TGTCTTGGGTTCGCCAGACTCCGGAGAAGAGGCTGGAGTGGGTCGCAACC

ATTAGTGGTGGTGGTCGTTACACCTATTATCCAGACAGTGTGAAGGGGCG

ATTCACCATCTCCAGAGACAATGCCAAGAACAACCTGTACCTGCAAATGA

GCAGTCTGAGGTCTGAGGACACGGCCTTGTATTACTGTGCAAATAGGTAC

GACGTGGACTGGTTTGCTTACTGGGGCCAAGGGACTCTGGTCACTGTCTC

TGCA

SEQ ID NO: 24
EVNLVESGGGLVKPGGSLKLSCAASGFTFS<u>SYDMS</u>WVRQTPEKRLEWVA<u>T</u>

<u>ISGGGRYTYYPDSVKG</u>RFTISRDNAKNNLYLQMSSLRSEDTALYYCAN<u>RY</u>

<u>DVDWFAY</u>WGQGTLVTVSA

SEQ ID NO: 25
GATATTGTGCTAACTCAGTCTCCAGCCACCCTGTCTGTGACTCCAGGAGA

TAGCGTCAGTCTTTCCTGCAGGGCCAGCCAAAGTATTAGCAACAACCTAC

ACTGGTATCAACAAAAATCACATGAGTCTCCAAGGCTTCTCATCAAGTAT

GCTTCCCAGTCCATCTCTGGGATCCCCTCCAGGTTCAGTGGTAGTGGATC

AGGGACAGATTTCACTCTCAGTATCAACAGTGTGGAGACTGAAGATTTTG

GAATGTATTTCTGTCAACAGAGTAACAGCTGGCCGCTCACGTTCGGTGCT

GGGACCAAGCTGGAGCTGAAT

SEQ ID NO: 26
DIVLTQSPATLSVTPGDSVSLSC<u>RASQSISNNLH</u>WYQQKSHESPRLLIK<u>Y</u>

<u>ASQSIS</u>GIPSRFSGSGSGTDFTLSINSVETEDFGMYFC<u>QQSNSWPLT</u>FGA

GTKLELN

The sequence information of antibody No. 1-25 (mAb1-25) is as follows: the heavy chain variable region gene sequence is 351 bp in length, encoding 117 amino acid residues, the nucleotide sequence is shown in SEQ ID NO: 27, and the amino acid sequence is shown in SEQ ID NO: 28; the light chain variable region gene sequence is 321 bp in length, encoding 107 amino acid residues, the nucleotide sequence is shown in SEQ ID NO: 29, and the amino acid sequence is shown in SEQ ID NO: 30. The amino acid sequences were aligned in IgBLAST, both of which are consistent with the characteristics of the mouse IgG variable region gene. The amino acid sequences were aligned in IgBLAST, and the light chain and heavy chain of antibodies No. 1-15 and 1-25 were consistent with the characteristics of the mouse IgG variable region gene.

SEQ ID NO: 27
GAAGTGAAGCTGGTGGAGTCTGGGGGAGACTTAGTGAAGCCTGGAGGGTC

CCTGAAACTCTCCTGTGTAGCCTCTGGATTCGCTTTCAGTAGCTATGACA

TGTCTTGGGTTCGCCAAACTCCGGAGAAGCGGCTGGAGTGGGTCGCTACC

ATTAGTGGTGGTGGTCGTTACACCTACTATCCAGACACTGTGAAGGGCCG

ATTCACCATCTCCAGAGACAATGCCAGGAACACCCACTACCTGCAAATGA

GCAGTCTGAGGTCTGAGGACACGGCCCTCTATTTTTGTGCAAGTCCTTAC

GGCGGTTACTTCGATGTCTGGGGCGCAGGGACCACGGTCACCGTCTCCTC

A

SEQ ID NO: 28
EVKLVESGGDLVKPGGSLKLSCVASGFAFS<u>SYDMS</u>WVRQTPEKRLEWVA<u>T</u>

<u>ISGGGRYTYYPDTVKG</u>RFTISRDNARNTHYLQMSSLRSEDTALYFCAS<u>PY</u>

<u>GGYFD</u>VWGAGTTVTVSS

SEQ ID NO: 29
GATATTGTGCTAACTCAGTCTCCAGCCACCCTGTCTGTGACTCCGGGAGC

TAGAGTCAGTCTTTCCTGCAGGGCCAGTCAAAGTATTAGCAACTTCCTAC

ACTGGTATCAACAAAAATCACATGAGTCTCCAAGGCTTCTCATCAAATAT

GCTTCTCAGTCCATTTCTGGGATCCCCTCCAGGTTCAGTGGCAGTGGATC

AGGGACAGATTTCACTCTCAGTATCAGCAGTGTGGAGACTGAAGATTTTG

GAATGTATTTCTGTCAACAGAGTAACAGCTGGCCTCATACGTTCGGTGCT

GGGACCAAGCTGGAGCTGAAA

SEQ ID NO: 30
DIVLTQSPATLSVTPGARVSLSC<u>RASQSISNFLH</u>WYQQKSHESPRLLIK<u>Y</u>

<u>ASQSIS</u>GIPSRFSGSGSGTDFTLSISSVETEDFGMYFC<u>QQSNSWPHT</u>FGA

GTKLELK

Example 6. Humanization of Murine Anti-Human PD-1 Monoclonal Antibodies

The amino acid sequences of the heavy chain variable region and the light chain variable region in Example 5 were analyzed, and three complementarity-determining regions (CDRs) and four frame regions (FRs) of the antibodies No. 1-15 and 1-25 (mAb1-15 and mAb1-25) were identified according to the Kabat rule.

Wherein, the amino acid sequences of the heavy chain complementarity determining regions of clone No. 1-15 are H-CDR1 (or CDRH1): SYDMS (SEQ ID NO: 13), H-CDR2: TISGGGRYTYYPDSVKG (SEQ ID NO: 14), and H-CDR3: RYDVDWFAY (SEQ ID NO: 15), the amino acid sequences of the light chain complementarity determining regions are L-CDR1: RASQSISNNLH (SEQ ID NO: 16), L-CDR2: YASQSIS (SEQ ID NO: 17), and L-CDR3: QQSNSWPLT (SEQ ID NO): 18).

SEQ ID NO: 13
SYDMS

SEQ ID NO: 14
TISGGGRYTYYPDSVKG

-continued

RYDVDWFAY                                    SEQ ID NO: 15

RASQSISNNLH                                  SEQ ID NO: 16

YASQSIS                                      SEQ ID NO: 17

QQSNSWPLT                                    SEQ ID NO: 18

Wherein, the amino acid sequences of the heavy chain complementarity determining regions of clone No. 1-25 are H-CDR1: SYDMS (SEQ ID NO: 1), H-CDR2: TISGG-GRYTYYPDTVKG (SEQ ID NO: 2), and H-CDR3: PYG-GYFDV (SEQ ID NO: 3), the amino acid sequences of the light chain complementarity determining regions are L-CDR1: RASQSISNFLH (SEQ ID NO: 4), L-CDR2: YASQSIS (SEQ ID NO: 5), and L-CDR3: QQSNSWPHT (SEQ ID NO: 6).

SYDMS                                         SEQ ID NO: 1

TISGGGRYTYYPDTVKG                             SEQ ID NO: 2

PYGGYFDV                                      SEQ ID NO: 3

RASQSISNFLH                                   SEQ ID NO: 4

YASQSIS                                       SEQ ID NO: 5

QQSNSWPHT                                     SEQ ID NO: 6

For antibody No. 1-15, by homology comparison with human IgG germline sequence at NCBI IgBLAST, IGHV3-7*03 was selected as the heavy chain CDR graft template, the heavy chain CDRs of murine antibody No. 1-15 were transplanted into the template to construct a heavy chain CDR-grafted antibody. Similarly, by homology comparison with human IgG germline sequence, IGKV3-11*01 was selected as the light chain CDR graft template, and the light chain CDRs of murine antibody No. 1-15 were transplanted into the template to construct a light chain CDR-grafted antibody. Meanwhile, on this basis, some amino acid sites in the framework region were subjected to back mutation. The back mutation was to mutate certain amino acids in the human framework region into amino acids at the same position in the mouse framework region. When back mutation was performed, the amino acid sequence was encoded by Kabat numbering system and the position was indicated by Kabat numbering. Preferably, for the heavy chain variable region sequence, G at position 44 by Kabat numbering was back mutated to R, and R at position 94 was back mutated to N. For the light chain variable region sequence, Y at position 49 by Kabat numbering was back mutated to K, and Y at position 87 was back mutated to F. The above variable region gene sequences were codon-optimized and synthesized according to the codon usage preference of *Cricetulus griseus* by Suzhou Genewiz Company.

The heavy chain variable region gene sequence of the finally obtained humanized antibody No. 1-15 (mAb1-15-humanized) is 354 bp in length, encoding 118 amino acid residues, and the nucleotide sequence is shown in SEQ ID NO:31, the amino acid sequence is shown in SEQ ID NO: 19, the heavy chain full length sequence is shown in SEQ ID NO: 20; the light chain variable region gene sequence of the humanized antibody No. 1-15 is 321 bp in length, encoding 107 amino acid residues, the nucleotide sequence is shown in SEQ ID NO: 32, the amino acid sequence is shown in SEQ ID NO: 21, and the light chain full length sequence is shown in SEQ ID NO: 22.

SEQ ID NO: 31
GAGGTGCAGCTGGTGGAGAGCGGCGGCGGCCTGGTGCAGCCCGGCGGCAG
CCTGAGGCTGAGCTGCGCCGCCAGCGGCTTCACCTTCAGCAGCTACGACA
TGAGCTGGGTGAGGCAGGCCCCCGGCAAGAGGCTGGAGTGGGTGGCCACC
ATCAGCGGCGGCGGCAGGTACACCTACTACCCCGACAGCGTGAAGGGCAG
GTTCACCATCAGCAGGGACAACGCCAAGAACAGCCTGTACCTGCAGATGA
ACAGCCTGAGGGCCGAGGACACCGCCGTGTACTACTGCGCCAACAGGTAC
GACGTGGACTGGTTCGCCTACTGGGGCCAGGGCACCCTGGTGACCGTGAG
CAGC

SEQ ID NO: 19
EVQLVESGGGLVQPGGSLRLSCAASGFTFS<u>SYDMS</u>WVRQAPGKRLEWVA<u>T</u>
<u>ISGGGRYTYYPDS</u>VKGRFTISRDNAKNSLYLQMNSLRAEDTAVYYCAN<u>RY</u>
<u>DVDWFAY</u>WGQGTLVTVSS

SEQ ID NO: 32
GAGATCGTGCTGACCCAGAGCCCCGCCACCCTGAGCCTGAGCCCCGGCGA
GAGGGCCACCCTGAGCTGCAGGGCCAGCCAGAGCATCAGCAACAACCTGC
ACTGGTACCAGCAGAAGCCCGGCCAGGCCCCCAGGCTGCTGATCAAGTAC
GCCAGCCAGAGCATCAGCGGCATCCCCGCCAGGTTCAGCGGCAGCGGCAG
CGGCACCGACTTCACCCTGACCATCAGCAGCCTGGAGCCCGAGGACTTCG
CCGTGTACTTCTGCCAGCAGAGCAACAGCTGGCCCCTGACCTTCGGCCAG
GGCACCAAGGTGGAGATCAAG

SEQ ID NO: 21
EIVLTQSPATLSLSPGERATLSC<u>RASQSISNNLH</u>WYQQKPGQAPRLLIK<u>Y</u>
<u>ASQSIS</u>GIPARFSGSGSGTDFTLTISSLEPEDFAVYFC<u>QQSNSWPLT</u>FGQ
GTKVEIK

For antibody No. 1-25, by homology comparison with human IgG germline sequence at NCBI IgBLAST, IGHV3-7*03 was selected as the heavy chain CDR graft template, the heavy chain CDRs of murine antibody No. 1-25 were transplanted into the template to construct a heavy chain CDR-grafted antibody. Similarly, by homology comparison with human IgG germline sequence, IGKV3-11*01 was selected as the light chain CDR graft template, and the light chain CDRs of murine antibody No. 1-25 were transplanted into the template to construct a light chain CDR-grafted antibody. Meanwhile, on this basis, some amino acid sites in the framework region were subjected to back mutation. The back mutation was to mutate certain amino acids in the human framework region into amino acids at the same position in the mouse framework region. When back mutation was performed, the amino acid sequence was encoded by Kabat numbering system and the position was indicated by Kabat numbering. Preferably, for the heavy chain variable region sequence, Q at position 3 by Kabat numbering was back mutated to K, G at position 44 was back mutated to R, L at position 78 was back mutated to H, Y at position 91 was back mutated to F, R at position 94 was back mutated to S. For the light chain variable region sequence, Y at position 49 by Kabat numbering was back mutated to K, and Y at position 87 was back mutated to F. The above variable region gene sequences were codon-optimized and synthesized according to the codon usage preference of *Cricetulus griseus* by Suzhou Genewiz Company.

The heavy chain variable region gene sequence of the finally obtained humanized antibody No. 1-25 (mAb1-25-Humanized) is 351 bp in length, encoding 117 amino acid residues, and the nucleotide sequence is shown in SEQ ID NO:33, the amino acid sequence is shown in SEQ ID NO: 7; the light chain variable region gene sequence of humanized antibody No. 1-25 is 321 bp in length, encoding 107 amino acid residues, and the nucleotide sequence is shown in SEQ ID NO: 34, the amino acid sequence is shown in SEQ ID NO: 9.

SEQ ID NO: 33
GAAGTCAAACTCGTGGAGTCCGGCGGAGGCCTCGTTCAACCAGGTGGATC
TCTTCGTTTGTCCTGCGCAGCATCAGGATTCGCTTTCTCCAGCTACGACA
TGAGCTGGGTCCGACAGGCTCCTGGAAAGAGGCTGGAATGGGTTGCTACT
ATCAGCGGCGGTGGTAGATATACTTATTACCCCGATACCGTAAAGGGGAG
GTTCACCATTAGTCGCGATAACGCCAAAAATTCACACTACCTGCAGATGA
ACTCTCTGCGGGCCGAGGACACCGCCGTGTACTTTTGTGCCAGTCCCTAT
GGCGGGTATTTTGACGTGTGGGGCCAGGGGACACTGGTGACTGTGAGTTC
T

SEQ ID NO: 7
EVKLVESGGGLVQPGGSLRLSCAASGFAFS<u>SYDMS</u>WVRQAPGKRLEWVA<u>T</u>
<u>ISGGGRYTYYPDTVK</u>GRFTISRDNAKNSHYLQMNSLRAEDTAVYFCAS<u>PY</u>
<u>GGYFDV</u>WGQGTLVTVSS

SEQ ID NO: 34
GAGATCGTCCTTACCCAATCACCAGCAACCTTGTCACTGTCACCAGGTGA
AAGAGCAACCCTCAGTTGTAGGGCTAGTCAGAGTATCTCCAACTTCCTGC
ACTGGTACCAGCAGAAGCCTGGACAGGCCCCTCGGTTGCTCATTAAGTAC
GCCTCTCAATCTATCAGCGGAATCCCCGCTCGCTTTTCTGGCTCTGGCTC
CGGGACTGATTTCACTCTGACAATTTCCAGCCTGGAACCCGAGGACTTTG
CCGTTTATTTTTGCCAGCAGAGCAATAGCTGGCCCCATACATTCGGGCAG
GGCACAAAAGTGGAGATAAAA

SEQ ID NO: 9
EIVLTQSPATLSLSPGERATLSC<u>RASQSISNFLH</u>WYQQKPGQAPRLLIK<u>Y</u>
<u>ASQSISG</u>IPARFSGSGSGTDFTLTISSLEPEDFAVYFC<u>QQSNSWPHT</u>FGQ
GTKVEIK

The humanized heavy chain variable region sequence of the above artificially synthesized antibody No. 1-15 (mAb1-15-Humanized) was ligated to the human immunoglobulin IgG4 constant region (the nucleotide sequence of the human immunoglobulin IgG4 constant region is shown in SEQ ID NO: 35, the amino acid sequence is shown in SEQ ID NO: 36) to construct the complete humanized heavy chain of antibody No. 1-15 (the nucleotide sequence is shown in SEQ ID NO: 37, the amino acid sequence is shown in SEQ ID NO: 20), the light chain variable region was ligated to the human immunoglobulin Kappa chain constant region (the nucleotide sequence of the human immunoglobulin Kappa chain constant region is shown in SEQ ID NO: 38, the amino acid sequence is shown in SEQ ID NO: 39) to construct the complete humanized light chain of antibody No. 1-15 (the nucleotide sequence is shown in SEQ ID NO: 40, the amino acid sequence is shown in SEQ ID NO: 22).

SEQ ID NO: 35
GCAAGTACCAAGGGACCTAGTGTTTTCCCTCTTGCACCTTGCTCCAGGTC
AACATCAGAGTCCACAGCTGCTCTTGGATGTCTCGTTAAGGACTACTTCC
CAGAGCCAGTTACCGTATCCTGGAACTCCGGAGCTTTGACAAGCGGCGTT
CATACATTCCCAGCTGTGTTGCAGAGTTCTGGGTTGTACAGTTTGAGCTC
AGTGGTGACCGTGCCTTCATCTTCTTTGGGCACTAAGACCTACACCTGCA
ACGTGGATCACAAGCCAAGCAACACCAAGGTGGATAAGAGGGTGGAGTCC
AAGTACGGCCCACCATGTCCTCCATGTCCAGCCCCTGAATTTTTGGGCGG
GCCTTCTGTCTTTCTGTTTCCTCCTAAACCTAAAGATACCCTGATGATCA
GCCGCACACCCGAAGTCACTTGTGTGGTCGTGGATGTGTCTCAGGAAGAT
CCCGAAGTGCAGTTTAACTGGTATGTCGATGGCGTGGAAGTGCATAATGC
CAAAACTAAGCCCCGCGAAGAACAGTTCAACAGCACTTATCGGGTCGTGT
CTGTGCTCACAGTCCTCCATCAGGATTGGCTGAATGGGAAAGAATATAAG
TGCAAGGTGAGCAATAAGGGCCTCCCCAGCAGCATCGAGAAGACTATTAG
CAAAGCCAAAGGGCAGCCACGGGAACCCCAGGTGTACACTCTGCCCCCCT
CTCAGGAGGAGATGACTAAAAATCAGGTCTCTCTGACTTGTCTGGTGAAA
GGGTTTTATCCCAGCGACATTGCCGTGGAGTGGGAGTCTAATGGCCAGCC
CGAGAATAATTATAAGACAACTCCCCCCGTCCTGGACTCTGACGGCAGCT
TTTTCCTGTATTCTCGGCTGACAGTGGACAAAAGTCGCTGGCAGGAGGGC
AATGTCTTTAGTTGCAGTGTCATGCATGAGGCCCTGCACAATCACTATAC
ACAGAAAGCCTGTCTCTGAGTCTGGGCAAA

SEQ ID NO: 36
ASTKGPSVFPLAPCSRSTSESTAALGCLVKDYFPEPVTVSWNSGALTSGV
HTFPAVLQSSGLYSLSSVVTVPSSSLGTKTYTCNVDHKPSNTKVDKRVES
KYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYK
CKVSNKGLPSSIEKTISKAKGQPREPQVYTLPPSQEEMTKNQVSLTCLVK
GFYPSDIAVEWESNGQPENNYKTTPPVLDSDGSFFLYSRLTVDKSRWQEG
NVFSCSVMHEALHNHYTQKSLSLSLGK

SEQ ID NO: 37
GAGGTGCAGCTGGTGGAGAGCGGCGGCGGCCTGGTGCAGCCCGGCGGCAG
CCTGAGGCTGAGCTGCGCCGCCAGCGGCTTCACCTTCAGCAGCTACGACA
TGAGCTGGGTGAGGCAGGCCCCCGGCAAGAGGCTGGAGTGGGTGGCCACC
ATCAGCGGCGGCGGCAGGTACACCTACTACCCCGACAGCGTGAAGGGCAG
GTTCACCATCAGCAGGGACAACGCCAAGAACAGCCTGTACCTGCAGATGA
ACAGCCTGAGGGCCGAGGACACCGCCGTGTACTACTGCGCCAACAGGTAC
GACGTGGACTGGTTCGCCTACTGGGGCCAGGGCACCCTGGTGACCGTGAG

```
CAGCGCAAGTACCAAGGGACCTAGTGTTTTCCCTCTTGCACCTTGCTCCA
GGTCAACATCAGAGTCCACAGCTGCTCTTGGATGTCTCGTTAAGGACTAC
TTCCCAGAGCCAGTTACCGTATCCTGGAACTCCGGAGCTTTGACAAGCGG
CGTTCATACATTCCCAGCTGTGTTGCAGAGTTCTGGGTTGTACAGTTTGA
GCTCAGTGGTGACCGTGCCTTCATCTTCTTTGGGCACTAAGACCTACACC
TGCAACGTGGATCACAAGCCAAGCAACACCAAGGTGGATAAGAGGGTGGA
GTCCAAGTACGGCCCACCATGTCCTCCATGTCCAGCCCCTGAATTTTTGG
GCGGGCCTTCTGTCTTTCTGTTTCCTCCTAAACCTAAAGATACCCTGATG
ATCAGCCGCACACCCGAAGTCACTTGTGTGGTCGTGGATGTGTCTCAGGA
AGATCCCGAAGTGCAGTTTAACTGGTATGTCGATGGCGTGGAAGTGCATA
ATGCCAAAACTAAGCCCCGCGAAGAACAGTTCAACAGCACTTATCGGGTC
GTGTCTGTGCTCACAGTCCTCCATCAGGATTGGCTGAATGGGAAAGAATA
TAAGTGCAAGGTGAGCAATAAGGGCCTCCCCAGCAGCATCGAGAAGACTA
TTAGCAAAGCCAAAGGGCAGCCACGGGAACCCCAGGTGTACACTCTGCCC
CCCTCTCAGGAGGAGATGACTAAAAATCAGGTCTCTCTGACTTGTCTGGT
GAAAGGGTTTTATCCCAGCGACATTGCCGTGGAGTGGGAGTCTAATGGCC
AGCCCGAGAATAATTATAAGACAACTCCCCCCGTCCTGGACTCTGACGGC
AGCTTTTTCCTGTATTCTCGGCTGACAGTGGACAAAAGTCGCTGGCAGGA
GGGCAATGTCTTTAGTTGCAGTGTCATGCATGAGGCCCTGCACAATCACT
ATACACAGAAAAGCCTGTCTCTGAGTCTGGGCAAA
```

SEQ ID NO: 20
EVQLVESGGGLVQPGGSLRLSCAASGFTFSSYDMSWVRQAPGKRLEWVAT
ISGGGRYTYYPDSVKGRFTISRDNAKNSLYLQMNSLRAEDTAVYYCANRY
DVDWFAYVVGQGTLVTVSSASTKGPSVFPLAPCSRSTSESTAALGCLVKD
YFPEPVTVSWNSGALTSGVHTFPAVLQSSGLYSLSSVVTVPSSSLGTKTY
TCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYR
VVSVLTVLHQDWLNGKEYKCKVSNKGLPSSIEKTISKAKGQPREPQVYTL
PPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLGK

SEQ ID NO: 38
```
CGCACTGTGGCTGCCCCCAGTGTTTTCATATTTCCCCCCAGTGATGAGCA
ACTGAAGTCCGGCACAGCCTCTGTTGTATGTCTGCTGAATAATTTTTATC
CACGGGAGGCCAAGGTGCAGTGGAAGGTGGACAATGCCCTGCAGTCTGGG
AACTCTCAAGAGAGTGTGACAGAGCAGGACAGTAAAGACAGCACCTATAG
CCTCAGCAGCACCCTGACCCTGTCTAAAGCCGACTATGAAAAACACAAAG
TGTATGCCTGCGAAGTGACCCATCAGGGGCTCAGCTCTCCCGTTACCAAG
AGCTTTAACCGAGGCGAATGT
```

SEQ ID NO: 39
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC

SEQ ID NO: 40
```
GAGATCGTGCTGACCCAGAGCCCCGCCACCCTGAGCCTGAGCCCCGGCGA
GAGGGCCACCCTGAGCTGCAGGGCCAGCCAGAGCATCAGCAACAACCTGC
ACTGGTACCAGCAGAAGCCCGGCCAGGCCCCCAGGCTGCTGATCAAGTAC
GCCAGCCAGAGCATCAGCGGCATCCCCGCCAGGTTCAGCGGCAGCGGCAG
CGGCACCGACTTCACCCTGACCATCAGCAGCCTGGAGCCCGAGGACTTCG
CCGTGTACTTCTGCCAGCAGAGCAACAGCTGGCCCCTGACCTTCGGCCAG
GGCACCAAGGTGGAGATCAAGCGCACTGTGGCTGCCCCCAGTGTTTTCAT
ATTTCCCCCCAGTGATGAGCAACTGAAGTCCGGCACAGCCTCTGTTGTAT
GCTGCTGAATAATTTTTATCCACGGGAGGCCAAGGTGCAGTGGAAGGTGG
ACAATGCCCTGCAGTCTGGGAACTCTCAAGAGAGTGTGACAGAGCAGGAC
AGTAAAGACAGCACCTATAGCCTCAGCAGCACCCTGACCCTGTCTAAAGC
CGACTATGAAAAACACAAAGTGTATGCCTGCGAAGTGACCCATCAGGGGC
TCAGCTCTCCCGTTACCAAGAGCTTTAACCGAGGCGAATGT
```

SEQ ID NO: 22
EIVLTQSPATLSLSPGERATLSCRASQSISNNLHWYQQKPGQAPRLLIKY
ASQSISGIPARFSGSGSGTDFTLTISSLEPEDFAVYFCQQSNSWPLTFGQ
GTKVEIKRTVAAPSVFIFPPSDEQLKSGTASVVCLLNNFYPREAKVQWKV
DNALQSGNSQESVTEQDSKDSTYSLSSTLTLSKADYEKHKVYACEVTHQG
LSSPVTKSFNRGEC

The humanized heavy chain variable region sequence of the above artificially synthesized antibody No. 1-25 (mAb1-25-Humanized) was ligated to the human immunoglobulin IgG4 constant region (the nucleotide sequence is shown in SEQ ID NO: 35, the amino acid sequence is shown in SEQ ID NO: 36) to construct the complete humanized heavy chain of antibody No. 1-25 (the nucleotide sequence is shown in SEQ ID NO: 11, the amino acid sequence is shown in SEQ ID NO: 8), the light chain variable region was ligated to the human immunoglobulin Kappa chain constant region (the nucleotide sequence is shown in SEQ ID NO: 38, the amino acid sequence is shown in SEQ ID NO: 39) to construct the complete humanized light chain of antibody No. 1-25 (the nucleotide sequence is shown in SEQ ID NO: 12, the amino acid sequence is shown in SEQ ID NO: 10).

SEQ ID NO: 11
```
GAAGTCAAACTCGTGGAGTCCGGCGGAGGCCTCGTTCAACCAGGTGGATC
TCTTCGTTTGTCCTGCGCAGCATCAGGATTCGCTTTCTCCAGCTACGACA
TGAGCTGGGTCCGACAGGCTCCTGGAAAGAGGCTGGAATGGGTTGCTACT
ATCAGCGGCGGTGGTAGATATACTTATTACCCCGATACCGTAAAGGGGAG
GTTCACCATTAGTCGCGATAACGCCAAAAATTCACACTACCTGCAGATGA
ACTCTCTGCGGGCCGAGGACACCGCCGTGTACTTTTGTGCCAGTCCCTAT
GGCGGGTATTTTGACGTGTGGGGCCAGGGGACACTGGTGACTGTGAGTTC
TGCAAGTACCAAGGGACCTAGTGTTTTCCCTCTTGCACCTTGCTCCAGGT
CAACATCAGAGTCCACAGCTGCTCTTGGATGTCTCGTTAAGGACTACTTC
CCAGAGCCAGTTACCGTATCCTGGAACTCCGGAGCTTTGACAAGCGGCGT
TCATACATTCCCAGCTGTGTTGCAGAGTTCTGGGTTGTACAGTTTGAGCT
```

-continued

CAGTGGTGACCGTGCCTTCATCTTCTTTGGGCACTAAGACCTACACCTGC

AACGTGGATCACAAGCCAAGCAACACCAAGGTGGATAAGAGGGTGGAGTC

CAAGTACGGCCCACCATGTCCTCCATGTCCAGCCCCTGAATTTTTGGGCG

GGCCTTCTGTCTTTCTGTTTCCTCCTAAACCTAAAGATACCCTGATGATC

AGCCGCACACCCGAAGTCACTTGTGTGGTCGTGGATGTGTCTCAGGAAGA

TCCCGAAGTGCAGTTTAACTGGTATGTCGATGGCGTGGAAGTGCATAATG

CCAAAACTAAGCCCCGCGAAGAACAGTTCAACAGCACTTATCGGGTCGTG

TCTGTGCTCACAGTCCTCCATCAGGATTGGCTGAATGGGAAAGAATATAA

GTGCAAGGTGAGCAATAAGGGCCTCCCCAGCAGCATCGAGAAGACTATTA

GCAAAGCCAAAGGGCAGCCACGGGAACCCCAGGTGTACACTCTGCCCCCC

TCTCAGGAGGAGATGACTAAAAATCAGGTCTCTCTGACTTGTCTGGTGAA

AGGGTTTTATCCCAGCGACATTGCCGTGGAGTGGGAGTCTAATGGCCAGC

CCGAGAATAATTATAAGACAACTCCCCCCGTCCTGGACTCTGACGGCAGC

TTTTTCCTGTATTCTCGGCTGACAGTGGACAAAAGTCGCTGGCAGGAGGG

CAATGTCTTTAGTTGCAGTGTCATGCATGAGGCCCTGCACAATCACTATA

CACAGAAAAGCCTGTCTCTGAGTCTGGGCAAA

SEQ ID NO: 8
EVKLVESGGGLVQPGGSLRLSCAASGFAFSSYDMSWVRQAPGKRLEWVAT

ISGGGRYTYYPDTVKGRFTISRDNAKNSHYLQMNSLRAEDTAVYFCASPY

GGYFDVWGQGTLVTVSSASTKGPSVFPLAPCSRSTSESTAALGCLVKDYF

PEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMI

SRTPEVTCVVVDVSQEDPEVQFNWYVDGVEVHNAKTKPREEQFNSTYRVV

SVLTVLHQDWLNGKEYKCKVSNKGLPSSIEKTISKAKGQPREPQVYTLPP

SQEEMTKNQVSLTCLVKGFYPSDIAVEWESNGQPENNYKTTPPVLDSDGS

FFLYSRLTVDKSRWQEGNVFSCSVMHEALHNHYTQKSLSLSLGK

SEQ ID NO: 12
GAGATCGTCCTTACCCAATCACCAGCAACCTTGTCACTGTCACCAGGTGA

AAGAGCAACCCTCAGTTGTAGGGCTAGTCAGAGTATCTCCAACTTCCTGC

ACTGGTACCAGCAGAAGCCTGGACAGGCCCCTCGGTTGCTCATTAAGTAC

GCCTCTCAATCTATCAGCGGAATCCCCGCTCGCTTTTCTGGCTCTGGCTC

CGGGACTGATTTCACTCTGACAATTTCCAGCCTGGAACCCGAGGACTTTG

CCGTTTATTTTTGCCAGCAGAGCAATAGCTGGCCCCATACATTCGGGCAG

GGCACAAAAGTGGAGATAAAACGCACTGTGGCTGCCCCCAGTGTTTTCAT

ATTTCCCCCCAGTGATGAGCAACTGAAGTCCGGCACAGCCTCTGTTGTAT

GTCTGCTGAATAATTTTTATCCACGGGAGGCCAAGGTGCAGTGGAAGGTG

GACAATGCCCTGCAGTCTGGGAACTCTCAAGAGAGTGTGACAGAGCAGGA

CAGTAAAGACAGCACCTATAGCCTCAGCAGCACCCTGACCCTGTCTAAAG

CCGACTATGAAAAACACAAAGTGTATGCCTGCGAAGTGACCCATCAGGGG

CTCAGCTCTCCCGTTACCAAGAGCTTTAACGAGGCGAATGT

SEQ ID NO: 10
EIVLTQSPATLSLSPGERATLSCRASQSISNFLHWYQQKPGQAPRLLIKY

ASQSISGIPARFSGSGSGTDFTLTISSLEPEDFAVYFCQQSNSWPHTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

The genes of the above humanized light chain and heavy chain of antibody No. 1-15 were constructed into the pTT5 expression vector, and the constructed humanized light and heavy chain expression vectors of antibody No. 1-15 were combined and subjected to transient transfection and antibody expression by the HEK293 system (purchased from NRC Biotechnology Research Institute). HEK293 cells were cultured in Free Style 293 Expression Medium (purchased from Gibco). The plasmid was transferred into the cells by PEI transfection, and 5 days later, the cell supernatant was collected. Purified antibodies were obtained by Protein A affinity chromatography. Such expressed and purified intact antibody molecule was named mAb1-15-Humanized.

Similarly, the genes of the above humanized light chain and heavy chain of antibody No. 1-25 were constructed into the pTT5 expression vector, and the constructed 1-25 humanized light and heavy chain expression vectors were combined and subjected to transient transfection and antibody expression by the HEK293E system. HEK293 cells were cultured in FreeStyle 293 Expression Medium. HEK293 cells were cultured in Free Style 293 Expression Medium. The plasmid was transferred into the cells by PEI transfection, and 5 days later, the cell supernatant was collected. Purified antibodies were obtained by Protein A affinity chromatography. Such expressed and purified intact antibody molecule was named mAb1-25-Humanized.

In addition, the heavy chain variable region and the light chain variable region of murine antibodies No. 1-15 and 1-25 were spliced with human immunoglobulin IgG4 heavy chain constant region (nucleotide sequence is shown in SEQ ID NO: 35, the amino acid sequence is shown in SEQ ID NO: 36) and Kappa light chain constant region (nucleotide sequence is shown in SEQ ID NO: 38, amino acid sequence is shown in SEQ ID NO: 39) by overlapping PCR, respectively, to construct the corresponding expression vector, and the antibodies were expressed and purified by the above method. The chimeric antibodies obtained were named mAb1-15-Chimeric and mAb1-25-Chimeric, respectively.

Figure 2:
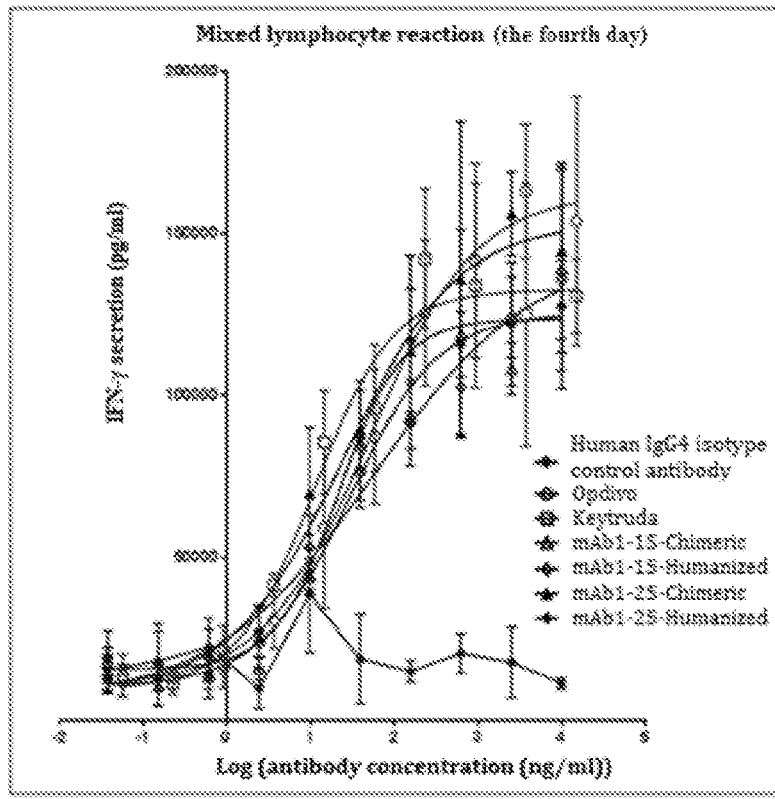
FIG. 2: Stimulation of IFN-γ secretion in MLR by the PD-1 antibody.
Figure 3:
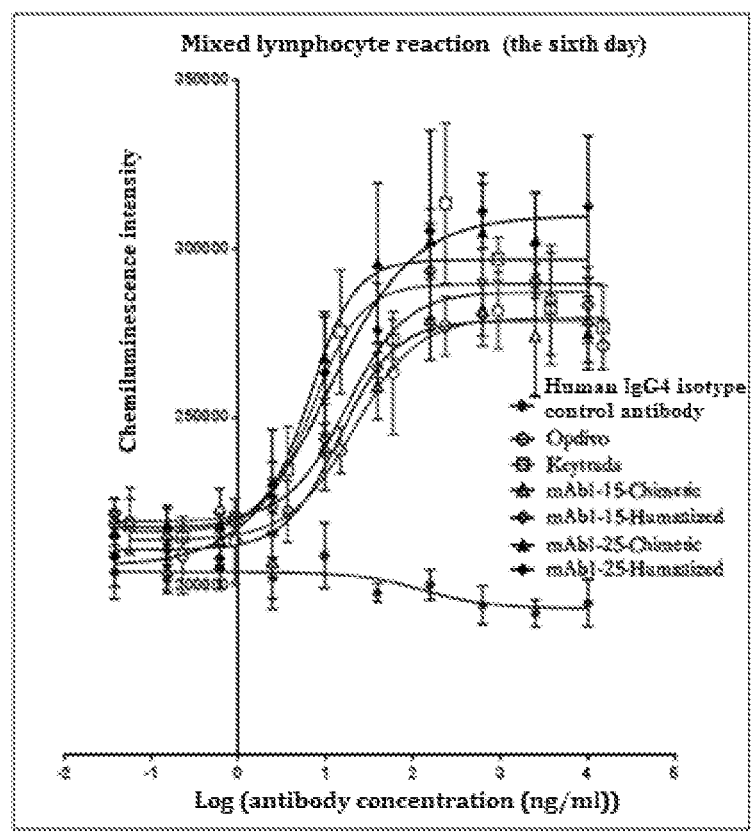
FIG. 3: Cell proliferation in MLR by the PD-1 antibody.

Example 7. Examination of Enhancement Effect on MLR by the Anti-Human PD-1 Monoclonal Antibodies of the Present Invention This example compared the functional activities between mAb1-15-Humanized and mAb1-25-Humanized in detail by the MLR (mixed lymphocyte reaction) method, and two positive control antibodies already on the market, Opdivo and Keytruda, were included. The procedure was carried out in accordance with Example 4, and the results of IL-2 secretion, IFN-γ secretion, and cell proliferation were analyzed. The results of the experiment are shown in FIG. 1-3. The human IgG4 isotype control antibody did not recognize human PD-1 and had no significant effect on MLR; while the positive control antibodies Opdivo and Keytruda could significantly enhance MLR and increase the secretion of IL-2, with EC50 (see Table 1) being 24.63 and 18.37 ng/ml, respectively; mAb1-15-Humanized and mAb1-25-Humanized of the present invention were also able to significantly enhance IL-2 secretion in MLR, with EC50 being 16.51 and 10.73 ng/ml, respectively; in addition, the ability of mAb1-15-Humanized and the corresponding chimeric antibody mAb1-15-Chimeric to enhance IL-2 secretion in MLR was similar (16.51 V.S. 23.56 ng/ml); the ability of mAb1-25-Humanized and the corresponding chimeric antibody mAb1-25-Chimeric to enhance IL-2 secretion in MLR was also similar (10.73 V.S. 9.953 ng/ml), indicating that the humanization of the murine antibody of the present invention was successful. The above results also indicate that mAb1-25-Humanized of the present invention is significantly stronger than the two positive control antibodies Opdivo and Keytruda in stimulating IL-2 secretion in MLR.

In addition, mAb1-15-Humanized and mAb1-25-Humanized of the present invention can also effectively stimulate the secretion of IFN-γ in MLR, and simultaneously stimulate the proliferation of T cells in MLR, and the EC50 is shown in the following table.

TABLE 1

Summary of EC50 data in FIG. 1-3

| EC50 (ng/ml) | Opdivo | Keytruda | mAb1-15-Chimeric | mAb1-15-Humanized | mAb1-25-Chimeric | mAb1-25-Humanized |
|---|---|---|---|---|---|---|
| IL-2 secretion (FIG. 1) | 24.63 | 18.37 | 23.56 | 16.51 | 9.953 | 10.73 |
| IFN-γ secretion (FIG. 2) | 50.02 | 11.12 | 28.42 | 55.71 | 25.42 | 21.36 |
| Cell proliferation (FIG. 3) | 20.93 | 6.985 | 14.64 | 17.24 | 6.686 | 10.60 |

Example 8. Determination of Affinity of Anti-Human PD-1 Monoclonal Antibodies of the Present Invention for Antigen The affinity of mAb1-15-Humanized and mAb1-25-Humanized for PD-1 was determined by Biacore T200 (GE healthcare). The first method was as follows: A CM5 sensor chip (GE healthcare) was activated by the Amine Coupling Kit (GE healthcare) and the Protein A/G fusion protein (Thermo Pierce) was immobilized on the chip with an amount of 2000 RU. FC3 (Flow cell 3) was a reference channel, and FC4 (Flow cell 4) was a sample channel. MAb1-15-Humanized, mAb1-25-Humanized or positive control antibodies (Opdivo and Keytruda) were captured on the FC4 channel, respectively, followed by injection of various concentrations of monovalent human PD-1 (purchased from Sino Biological Inc.). The cycling conditions were as follows: the analyte was injected at 50 μl/min for 4 min in all channels of the FC, the dissociation time was 20 min, 6M guanidine hydrochloride was injected at a rate of 10 μl/min for 30 s for surface regeneration, and finally the difference between the signals of the captured antibody and the signals of antibody-free controls as well as the affinity were calculated using Biacore T200 Evaluation Software Ver 1.0.

TABLE 2

Affinity of anti-human PD-1 monoclonal antibodies of the present invention for human PD-1 (first determination method)

| Sample name | Kon (M−1s−1) | Koff (s−1) | KD (M) |
|---|---|---|---|
| Opdivo | 8.05E+04 | 9.84E−04 | 1.22E−08 |
| Keytruda | 4.65E+05 | 2.57E−03 | 5.53E−09 |

TABLE 2-continued

Affinity of anti-human PD-1 monoclonal antibodies of the present invention for human PD-1 (first determination method)

| Sample name | Kon (M−1s−1) | Koff (s−1) | KD (M) |
|---|---|---|---|
| mAb1-15-Chimeric | 6.29E+04 | 1.48E−04 | 2.34E−09 |
| mAb1-15-Humanized | 2.73E+04 | 1.17E−04 | 4.28E−09 |
| mAb1-25-Chimeric | 1.79E+05 | 4.14E−05 | 2.31E−10 |
| mAb1-25-Humanized | 8.90E+04 | 2.61E−05 | 2.93E−10 |

The experimental results are shown in Table 2, mAb1-15-Humanized and mAb1-15-Chimeric of the present invention have similar affinity, and both of them have significantly higher affinity for PD-1 than the positive antibody Opdivo, which is similar to Keytruda. MAb1-25-Humanized and mAb1-25-Chimeric of the present invention have similar affinity, and both of them have significantly higher affinity for PD-1 than the positive antibodies Opdivo and Keytruda. The main advantage is that the dissociation is slower after binding to PD-1.

In this example, another method was used to determine the affinity of mAb1-15-Humanized and mAb1-25-Humanized for PD-1 by Biacore T200 (GE healthcare). The second determination method was as follows: PD-1-hFc in Example 1 was biotin-labelled using EZ-Link™ Sulfo-NHS-Biotin (Thermo Fisher Scientific), and the specific operation was carried out according to the instructions provided by the manufacturer. After labeling, the excess biotin labeling reagent was removed by dialysis; the aforementioned biotinylated PD-1-hFc fusion protein was immobilized on a chip using Sensor chip SA (GE healthcare). FC3 (Flow cell 3) was a reference channel, and FC4 (Flow cell 4) was a sample channel. Various concentrations of mAb1-15-Humanized, mAb1-25-Humanized or positive control antibody (Opdivo or Keytruda) were subsequently injected into the FC4 channel. The cycling conditions were as follows: the analyte was injected at 50 μl/min for 4 min in all channels of the FC, the dissociation time was 20 min, and finally the difference between signals of the captured antibody and the signals of antibody-free controls as well as the affinity were calculated using Biacore T200 Evaluation Software Ver 1.0.

TABLE 3

Determination of affinity of the anti-human PD-1 monoclonal antibodies of the present invention for human PD-1 (the second determination method)

| Sample name | Kon (M−1s−1) | Koff (s−1) | KD (M) |
|---|---|---|---|
| Opdivo | 1.13E+06 | 2.08E−04 | 1.84E−10 |
| Keytruda | 1.24E+06 | 2.53E−04 | 2.05E−10 |

TABLE 3-continued

Determination of affinity of the anti-human PD-1
monoclonal antibodies of the present invention
for human PD-1 (the second determination method)

| Sample name | Kon (M−1s−1) | Koff (s−1) | KD (M) |
| --- | --- | --- | --- |
| mAb1-15-Humanized | 7.64E+05 | 3.12E−05 | 4.08E−11 |
| mAb1-25-Humanized | 2.12E+06 | 1.99E−05 | 9.36E−12 |

The experimental results are shown in Table 3. The affinity of mAb 1-15-Humanized and mAb 1-25-Humanized of the present invention for PD-1 is significantly higher than those of the positive antibodies Opdivo and Keytruda, and the main advantage is that the dissociation is slower after binding to PD-1.

Example 9. Selectivity of the Anti-Human PD-1 Monoclonal Antibody of the Present Invention for PD-1 Family Members The protein molecules such as CD28, CTLA-4, and ICOS belong to the same family as PD-1, and the sequences have homology. To test whether the anti-human PD-1 monoclonal antibody of the present invention has cross-reactivity to the above molecules, the following experiment was carried out: An ELISA plate was coated with the protein molecules such as human PD-1-hFc, CD28-hFc, CTLA-4-hFc, ICOS-hFc (human PD-1-hFc was prepared as in Example 1, the extracellular domain sequence of CTLA-4 molecule was from http://www.uniprot.org/uniprot/P16410, CTLA-4-hFc was prepared according to the similar method to human PD-1-hFc in Example 1, CD28-hFc and ICOS-hFc were purchased from Sino Biological Inc.), respectively, at the same concentration of 2 μg/ml, 100 μl per well, overnight at 4° C.; washed twice with PBST (PBS containing 0.5% Tween-20) and patted dry. Each well was added with 200 μl of coating solution containing 1% BSA, and blocked at room temperature for 4 hours, then patted dry, and stored in a refrigerator at −20° C. until use. When detection was performed, 100 μl of serially-diluted mAb1-25-Humanized was added to each well of the ELISA plates, 3 replicate wells were set up, and incubated for 1 hour at room temperature; washed 3 times with PBST and then patted dry. 100 μl of HRP-labeled goat anti-human Fab antibody (purchased from Sigma) diluted 1:5000 with PBST was added and incubated at room temperature for 1 hour; washed 3 times with PBST and patted dry. 100 μl of chromogenic solution (ELISA chromogenic solution A and chromogenic solution B were mixed in a volume ratio of 1:1 before use) was added to each well, then 100 μl of 2M $H_2SO_4$ stop solution was added to each well to stop the reaction. The OD value of each well was immediately measured at a wavelength of 450 nm using a microplate reader (Molecular Device).

Figure 4:
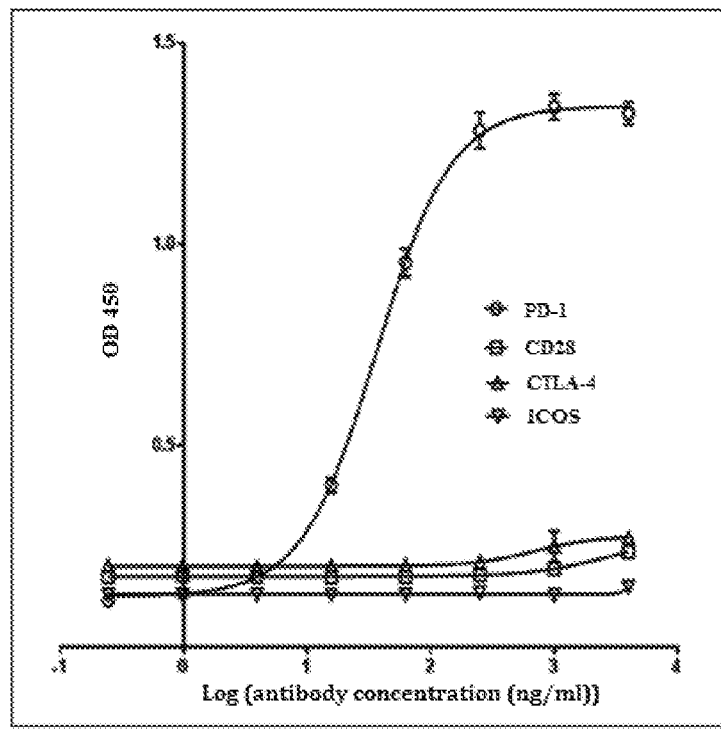
FIG. 4: Selection of PD-1 homologous members by mAb1-25-Humanized.

Experimental results are shown in FIG. 4. The mAb1-25-Humanized of the present invention specifically recognizes PD-1 without recognizing the protein molecules CD28, CTLA-4 and ICOS of the same family as PD-1, and the above results indicate that mAb1-25-Humanized of the present invention has good specificity.

Figure 5:
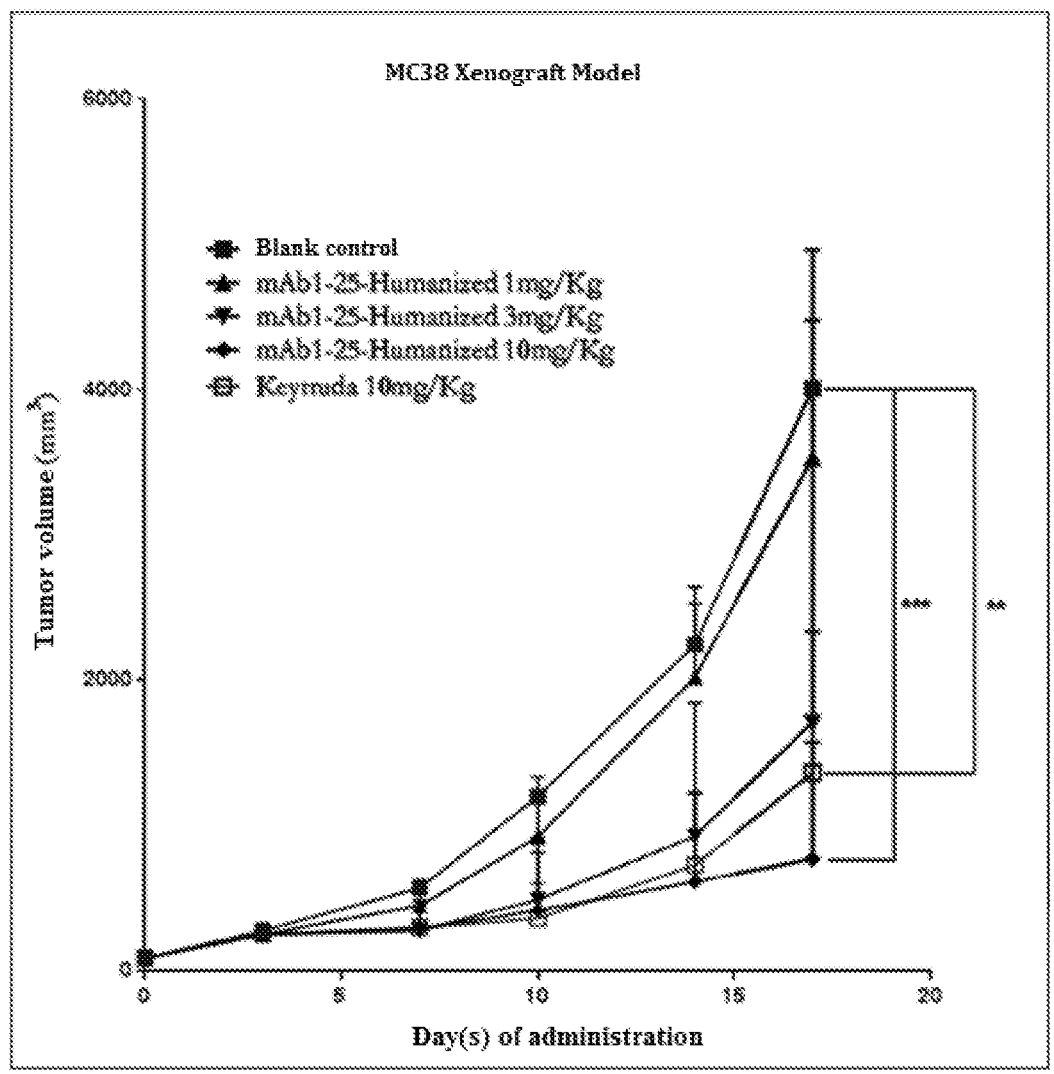
FIG. 5: Inhibition of mouse MC38 xenograft model by mAb1-25-Humanized.

Example 10. Evaluation of Anti-Tumor Effect of the Anti-Human PD-1 Monoclonal Antibody of the Present Invention in Mice Human PD-1 transgenic mice (germline background C57BL/6) and MC38 mouse colorectal cancer cells were purchased from the Shanghai Southern Model Biological Research Center, and the extracellular segment of human PD-1 gene was used to replace the homologous portion of the mouse in the transgenic mice, and thus the anti-human PD-1 monoclonal antibody of the present invention can recognize the PD-1 molecules in the transgenic mice, thereby functioning to activate the immune system, and achieving the purpose of inhibiting tumor growth. The specific implementation steps were as follows: MC38 cells were cultured in vitro, with DMEM containing 10% serum as medium (serum and medium were purchased from Gibco). The cultured MC38 cells were inoculated in human PD-1 transgenic mice, and inoculated subcutaneously with $1\times10^6$ cells per mice. When the tumor cells to be inoculated grew to a volume close to 100 $mm^3$, the animals were randomly grouped as follows: blank control group, 16 mice, injected with normal saline, as the control; mAb1-25-Humanized antibody group, having three dose groups of 1, 3, 10 mg/kg, respectively, 8 mice per group; positive control antibody Keytruda group, with a dose of 10 mg/kg, 8 mice. Subsequently, according to the above designed protocol, administration was carried out twice a week for three weeks, and the tumor volumes were measured twice a week. Finally, the measured tumor growth curves over time of each group are shown in FIG. 5.

The experimental results show that mAb1-25-Humanized of the present invention can inhibit tumor growth in vivo in a dose-dependent manner. Compared with the control group, mAb1-25-Humanized (10 mg/kg) can significantly inhibit the growth of MC38 xenograft tumors in mice (P=0.0007*), although Keytruda (10 mg/kg) may also significantly inhibit the growth of MC38 tumors (P=0.0012), the significance of Keytruda was less than that of mAb 1-25-Humanized of the present invention. In addition, in terms of tumor inhibition rate, compared with the control group, the tumor inhibition rate of mAb1-25-Humanized (10 mg/kg) group was 80.7%, whereas the tumor inhibition rate of Keytruda (10 mg/kg) was only 65.9%, it is obvious that mAb1-25-Humanized of the present invention can more effectively inhibit the growth of tumor cells in mice in vivo.

What is claimed is:

1. An anti-human PD-1 monoclonal antibody, characterized in that the anti-human PD-1 monoclonal antibody comprises:
   (a) a heavy chain complementarity determining region CDRH1, CDRH2, CDRH3, wherein the CDRH1 includes an amino acid sequence as recited in SEQ ID NO: 1, the CDRH2 includes an amino acid sequence as recited in SEQ ID NO: 2, and the CDRH3 includes an amino acid sequence as recited in SEQ ID NO: 3, or the CDRH1 includes an amino acid sequence as recited in SEQ ID NO: 13, the CDRH2 includes an amino acid sequence as recited in SEQ ID NO: 14, and the CDRH3 includes an amino acid sequence as recited in SEQ ID NO: 15, and
   (b) a light chain complementarity determining region CDRL1, CDRL2, CDRL3, wherein the CDRL1 includes an amino acid sequence as recited in SEQ ID NO: 4, the CDRL2 includes an amino acid sequence as recited in SEQ ID NO: 5, and the CDRL3 includes an amino acid sequence as recited in SEQ ID NO: 6, or the CDRL1 includes an amino acid sequence as recited in SEQ ID NO: 16, the CDRL2 includes an amino acid sequence as recited in SEQ ID NO: 17, and the CDRL3 includes an amino acid sequence as recited in SEQ ID NO: 18.

2. The anti-human PD-1 monoclonal antibody of claim 1, characterized in that, the anti-human PD-1 monoclonal antibody comprises a heavy chain variable region including an amino acid sequence as recited in SEQ ID NO: 7 or SEQ ID NO: 19 or SEQ ID NO: 24 or SEQ ID NO: 28, and a light chain variable region including an amino acid sequence as recited in SEQ ID NO: 9 or SEQ ID NO: 21 or SEQ ID NO: 26 or SEQ ID NO: 30.

3. The anti-human PD-1 monoclonal antibody of claim 2, characterized in that, the anti-human PD-1 monoclonal antibody comprises a heavy chain having the amino acid sequence as shown in SEQ ID NO: 8 or SEQ ID NO: 20, and a light chain having the amino acid sequence as shown in SEQ ID NO: 10 or SEQ ID NO: 22.

4. A nucleotide molecule, characterized in that, the nucleotide molecule encodes the anti-human PD-1 monoclonal antibody of claim 1.

5. The nucleotide molecule of claim 4, characterized in that, the nucleotide molecule comprises a nucleotide sequence as recited in SEQ ID NO: 23 or SEQ ID NO:27 or SEQ ID NO:31 or SEQ ID NO:33, and a nucleotide sequence as recited in SEQ ID NO:25 or SEQ ID NO:29 or SEQ ID NO:32 or SEQ ID NO:34, the nucleotide sequence recited in SEQ ID NO: 23 or SEQ ID NO:27 or SEQ ID NO:31 or SEQ ID NO:33 encodes the heavy chain variable region of the anti-human PD-1 monoclonal antibody, and the nucleotide sequence recited in SEQ ID NO:25 or SEQ ID NO:29 or SEQ ID NO:32 or SEQ ID NO:34 encodes the light chain variable region of the anti-human PD-1 monoclonal antibody.

6. The nucleotide molecule of claim 4, characterized in that, the nucleotide molecule comprises a nucleotide sequence as recited in SEQ ID NO: 11, and a nucleotide sequence as recited in SEQ ID NO: 12, the nucleotide sequence recited in SEQ ID NO: 11 encodes the heavy chain of the anti-human PD-1 monoclonal antibody, and the nucleotide sequence recited in SEQ ID NO: 12 encodes the light chain of the anti-human PD-1 monoclonal antibody, or
a nucleotide molecule comprises a nucleotide sequence as recited in SEQ ID NO: 37, and a nucleotide sequence as recited in SEQ ID NO: 40, the nucleotide sequence recited in SEQ ID NO: 37 encodes the heavy chain of the anti-human PD-1 monoclonal antibody, and the nucleotide sequence recited in SEQ ID NO: 40 encodes the light chain variable region of the anti-human PD-1 monoclonal antibody.

7. An expression vector, characterized in that, the expression vector comprises the nucleotide molecule of claim 4.

8. A host cell, characterized in that, the host cell comprises the expression vector of claim 7.

9. A preparation method of the anti-human PD-1 monoclonal antibody according to claim 1, characterized in that, the preparation method comprises the following steps:
a) under expression conditions, cultivating the host cell of claim 8 to express the anti-human PD-1 monoclonal antibody;
b) isolating and purifying the anti-human PD-1 monoclonal antibody of step a).

10. A composition, characterized in that, the composition comprises the anti-human PD-1 monoclonal antibody of claim 1 and a pharmaceutically acceptable carrier.

11. A method of treating a tumor in a subject, comprising administering an anti-human PD-1 monoclonal antibody as recited in claim 1 to the subject.

12. The method of claim 11, characterized in that, the tumor is colorectal cancer.

13. A nucleotide molecule, characterized in that, the nucleotide molecule encodes the anti-human PD-1 monoclonal antibody of claim 2.

14. A nucleotide molecule, characterized in that, the nucleotide molecule encodes the anti-human PD-1 monoclonal antibody of claim 3.

15. An expression vector, characterized in that, the expression vector comprises the nucleotide molecule of claim 5.

16. An expression vector, characterized in that, the expression vector comprises the nucleotide molecule of claim 6.

17. A preparation method of the anti-human PD-1 monoclonal antibody according to claim 2, characterized in that, the preparation method comprises the following steps:
a) under expression conditions, cultivating the host cell of claim 8 to express the anti-human PD-1 monoclonal antibody;
b) isolating and purifying the anti-human PD-1 monoclonal antibody of step a).

18. A preparation method of the anti-human PD-1 monoclonal antibody according to claim 3, characterized in that, the preparation method comprises the following steps:
a) under expression conditions, cultivating the host cell of claim 8 to express the anti-human PD-1 monoclonal antibody;
b) isolating and purifying the anti-human PD-1 monoclonal antibody of step a).

19. A composition, characterized in that, the composition comprises the anti-human PD-1 monoclonal antibody of claim 2 and a pharmaceutically acceptable carrier.

20. A composition, characterized in that, the composition comprises the anti-human PD-1 monoclonal antibody of claim 3 and a pharmaceutically acceptable carrier.

21. A method of treating a tumor in a subject, comprising administering an anti-human PD-1 monoclonal antibody as recited in claim 2 to the subject.

22. A method of treating a tumor in a subject, comprising administering an anti-human PD-1 monoclonal antibody as recited in claim 3 to the subject.

23. A method of treating a tumor in a subject, comprising administering an anti-human PD-1 monoclonal antibody and the composition as recited in claim 10 to the subject.

* * * * *